United States Patent
Albisetti et al.

(10) Patent No.: US 10,506,865 B2
(45) Date of Patent: Dec. 17, 2019

(54) DISPENSING DEVICE COMPRISING AN AQUEOUS COMPOSITION IN GEL OR THICK CREAM FORM

(71) Applicant: L'OREAL, Paris (FR)

(72) Inventors: Nicolas Albisetti, Saint Gratien (FR); Odile Aubrun, Antony (FR); Fabrice Springinsfeld, Fresnes (FR)

(73) Assignee: L'OREAL, Paris (FR)

( * ) Notice: Subject to any disclaimer, the term of this patent is extended or adjusted under 35 U.S.C. 154(b) by 54 days.

(21) Appl. No.: 14/767,610

(22) PCT Filed: Feb. 14, 2014

(86) PCT No.: PCT/EP2014/052926
§ 371 (c)(1),
(2) Date: Aug. 13, 2015

(87) PCT Pub. No.: WO2014/128061
PCT Pub. Date: Aug. 28, 2014

(65) Prior Publication Data
US 2015/0374098 A1 Dec. 31, 2015

(30) Foreign Application Priority Data
Feb. 21, 2013 (FR) ...................... 13 51477

(51) Int. Cl.
*A45D 40/26* (2006.01)
*B65D 35/00* (2006.01)
(Continued)

(52) U.S. Cl.
CPC .............. *A45D 40/26* (2013.01); *A61K 8/042* (2013.01); *A61K 8/25* (2013.01); *A61K 8/26* (2013.01);
(Continued)

(58) Field of Classification Search
CPC ........ A45D 40/26; B65D 35/00; A61Q 19/00; A61Q 15/00; A61K 8/042; A61K 8/927;
(Continued)

(56) References Cited

U.S. PATENT DOCUMENTS 5,924,605 A * 7/1999 Baudin .................. B65D 47/38
222/212

FOREIGN PATENT DOCUMENTS

WO WO-98/51185 A1 11/1998
WO WO2007068339 * 6/2007 ............. A61K 8/893
(Continued)

OTHER PUBLICATIONS

WO 2007/068339, English Translation, 2007, 57 pages. (Year: 2007).*

*Primary Examiner* — Trevor Love
(74) *Attorney, Agent, or Firm* — Polsinelli PC

(57) ABSTRACT

The present invention relates to a dispensing device comprising: a) a container comprising a deformable wall, and b) a composition stored in the container, and comprising, in a cosmetically acceptable medium: i) at least one aqueous phase, and ii) optionally at least one oily phase, iii) at least one structuring agent; the said composition having a stiffness modulus G*>5000 Pa, and c) a dispensing head closing off the container and comprising an application wall defining at least one product dispensing orifice which is a slit. The present invention also relates to a cosmetic process for treating and/or caring for human keratin materials, characterized in that it consists in applying to the surface of the keratin material a composition dispensed via the device as defined previously. The present invention also relates to a cosmetic process for treating human perspiration and/or perspiration-related body odour, which consists in applying (Continued)

to the surface of a human keratin material a composition dispensed via the device as defined previously.

15 Claims, 4 Drawing Sheets

(51) Int. Cl.

| | |
|---|---|
| *A61Q 19/00* | (2006.01) |
| *A61K 8/04* | (2006.01) |
| *A61K 8/92* | (2006.01) |
| *A61K 8/891* | (2006.01) |
| *A61K 8/86* | (2006.01) |
| *A61K 8/73* | (2006.01) |
| *A61K 8/60* | (2006.01) |
| *A61K 8/34* | (2006.01) |
| *A61K 8/26* | (2006.01) |
| *A61K 8/25* | (2006.01) |
| *A61Q 15/00* | (2006.01) |

(52) U.S. Cl.
    CPC .............. *A61K 8/342* (2013.01); *A61K 8/602* (2013.01); *A61K 8/732* (2013.01); *A61K 8/86* (2013.01); *A61K 8/891* (2013.01); *A61K 8/927* (2013.01); *A61Q 15/00* (2013.01); *A61Q 19/00* (2013.01); *B65D 35/00* (2013.01); *A61K 2800/592* (2013.01); *A61K 2800/87* (2013.01)

(58) Field of Classification Search
    CPC .......... A61K 8/891; A61K 8/86; A61K 8/732; A61K 8/602; A61K 8/342; A61K 8/26; A61K 8/25; A61K 2800/592; A61K 2800/87
    See application file for complete search history.

(56) References Cited

FOREIGN PATENT DOCUMENTS

| | | |
|---|---|---|
| WO | WO-2009/053898 A2 | 4/2009 |
| WO | WO-2010/115973 A1 | 10/2010 |

* cited by examiner

DISPENSING DEVICE COMPRISING AN AQUEOUS COMPOSITION IN GEL OR THICK CREAM FORM

CROSS REFERENCE TO RELATED APPLICATIONS

This application is a National Phase filing under 35 U.S.C. § 371 of PCT/EP2014/052926 filed on Feb. 14, 2014; and this application claims priority to Application No. 1351477 filed in France on Feb. 21, 2013. The entire contents of each application are hereby incorporated by reference.

The present invention relates to a dispensing device comprising:
a) a container comprising a deformable wall, and
b) a composition stored in the container, and comprising, in a cosmetically acceptable medium:
i) at least one aqueous phase, and
ii) optionally at least one oily phase,
iii) at least one structuring agent; the said composition having a stiffness modulus $G^*>5000$ Pa, and
c) a dispensing head closing off the container and comprising an application wall defining at least one product dispensing orifice which is a slit.

The present invention also relates to a cosmetic process for treating and/or caring for human keratin materials, characterized in that it consists in applying to the surface of the keratin material a composition dispensed via the device as defined previously.

The present invention also relates to a cosmetic process for treating human perspiration and/or perspiration-related body odour, which consists in applying to the surface of a human keratin material a composition comprising at least one deodorant active agent and/or antiperspirant active agent dispensed via the device as defined previously.

In the field of cosmetic skincare products, especially deodorant and antiperspirant products, various galenical categories may be defined: aerosols, sticks, creams, gels, soft solids, roll-ons, which suffer from consumer dissatisfaction, associated mainly with the working qualities of the products.

Roll-ons are a galenical form strongly represented on the market, but, like systems in direct emulsion form such as creams, they are fresh, fluid systems that have the drawbacks of being considered tacky, wetting and very slow-drying.

Antiperspirant anhydrous products in soft solid form exist on the market, as described especially in patent application WO 2012/084 522, delivered in stick-grates. They offer certain benefits in terms of application (softness, control of the applied dose), but may be perceived as being greasy, with a lack of freshness on application.

One of the objectives of the present invention is to look for products allying an immediate, soft, not wetting and non-sticky dry touch and which is effective in the application looked for without the inconveniences evoked previously.

The Appplicant noticed during her works that thick formulae of stiffness modulus $G^*>5000$ Pa, introduced into devices of distribution as a stick or a tube with deformable wall having a dispensing head closing off the container and comprising an application wall defining at least one product dispensing cylindrical orifice, did not allow to deliver, for a given dose, a completely satisfactory homogeneous distribution. Indeed, we observe, at the release of the opening, the formation of a sausage which leaves in a random way, outside the zone of application, what leads to an overflowing of the composition outside the zone to be treated, during the contact of the device with the surface of the keratinous substance.

There is thus a need to find cosmetic formulations for caring the human keratinous substances, in particular the skin, more particularily deodorant and\or antiperspirant products, having stiffness modulus $G^*>5000$ Pa and an adapted device of distribution which can produce at the release of the aforementioned device a homogeneous distribution of product which is concentrated in the zone of application without the drawbacks as evoked previously.

The Applicant has discovered that those objectives can be achieved with a dispensing device comprising:
a) a container comprising a deformable wall, and
b) a composition stored in the container, and comprising, in a cosmetically acceptable medium:
i) at least one aqueous phase, and
ii) optionally at least one oily phase,
iii) at least one structuring agent; the said composition having a stiffness modulus $G^*>5000$ Pa, and
c) a dispensing head closing off the container and comprising an application wall defining at least one product dispensing orifice which is a slit.

This discovery forms the basis of the invention.

The present invention relates to a dispensing device comprising:
a) a container comprising a deformable wall, and
b) a composition stored in the container, and comprising, in a cosmetically acceptable medium:
i) at least one aqueous phase, and
ii) optionally an oily phase,
iii) at least one structuring agent; the said composition having a stiffness modulus $G^*>5000$ Pa, and
c) a dispensing head closing off the container and comprising an application wall defining at least one product dispensing orifice which is a slit.

According to certain characteristics of the invention, each product dispensing orifice may have at any point a smallest transverse dimension of less than 1.3 mm, or even less than 1 mm, especially between 0.4 mm and 0.8 mm, or even between 0.5 mm and 0.7 mm.

The total extent of the orifices may be less than 5% or even less than 2.5% of the total extent of the surface of the application wall.

The application wall may be formed from a thermoplastic elastomer, such as a copolymer of ethylene and $\alpha$-olefin.

The container may be a deformable tube, this tube possibly comprising an inner pocket.

The present invention also relates to a cosmetic process for treating and/or caring for human keratin materials, characterized in that it consists in applying to the surface of the keratin material a composition dispensed via the device as defined previously.

The present invention also relates to a cosmetic process for treating human perspiration and/or perspiration-related body odour, which consists in applying to the surface of a human keratin material a composition comprising at least one deodorant active agent and/or antiperspirant active agent dispensed via the device as defined previously.

Other subjects of the invention will emerge later in the description.

The term "cosmetically acceptable" means compatible with the skin and/or its integuments or mucous membranes, having a pleasant colour, odour and feel and not causing any unacceptable discomfort (stinging, tautness or redness) liable to discourage the consumer from using this composition.

The term "human keratin materials" means the skin (body, face, area around the eyes), hair, eyelashes, eyebrows, body hair, nails, lips or mucous membranes.

The term "antiperspirant" means any substance which has the effect of reducing the flow of sweat and/or of reducing the sensation of moisture associated with human sweat, and/or of masking human sweat.

The term "deodorant active agent" refers to any substance that is capable of masking, absorbing, improving and/or reducing the unpleasant odour resulting from the decomposition of human sweat by bacteria.

The term "structuring agent" means any organic or mineral molecule, in the form of a simple compound, a dimer or a polymer (at least three monomers) which is capable of increasing the viscosity of at least one of the aqueous or oily liquid phases of the composition.

Stiffness Modulus

The compositions according to the invention are generally in the form of a gel or of thick creams and are characterized by a stiffness modulus G*>5000 Pa, and preferably G*>8000 Pa.

The corresponding measurements are taken at 25° C. using a Haake RS600 imposed-stress rheometer equipped with a plate-plate measuring body (60 mm diameter) fitted with an anti-evaporation device (bell jar). For each measurement, the sample is placed delicately in position and the measurements start 5 minutes after placing the sample in the air gap (2 mm). The test composition is then subjected to a stress ramp from $10^{-2}$ to $10^3$ Pa at a set frequency of 1 Hz.

Structuring Agent

The structuring agents in accordance with the invention may be chosen from hydrophilic structuring agents and lipophilic structuring agents, and mixtures thereof.

According to a particularly preferred form of the invention, the composition comprises a mixture of at least one hydrophilic structuring agent and of at least one lipophilic structuring agent.

The term "hydrophilic structuring agent" means any structuring agent that is water-soluble or water-dispersible in a liquid aqueous phase, which may be reflected by the fact that the structuring agent, introduced into an aqueous phase at 25° C., at a mass concentration equal to 1%, makes it possible to obtain a macroscopically uniform and thickened solution.

The term "lipophilic structuring agent" means any structuring agent that is liposoluble or lipodispersible in a liquid fatty phase, which may be reflected by the fact that the structuring agent, introduced into an oily phase at 25° C., at a mass concentration equal to 1%, makes it possible to obtain a macroscopically uniform and thickened oily phase.

The structuring agent(s) are preferably present in an amount ranging from 2% to 20% by weight and preferably from 2% to 15% by weight relative to the total weight of the composition. The amount will vary as a function of the desired texture and the intended cosmetic use.

A) Hydrophilic Structuring Agents

The hydrophilic structuring agents may be chosen from nonionic polymers, anionic polymers and cationic polymers, of natural or synthetic origin.

Among the hydrophilic structuring agents, mention may be made of:
a) water-soluble polysaccharides,
b) associative polymers,
c) non-associative, crosslinked and/or neutralized 2-acrylamido-2-methylpropanesulfonic acid polymers and copolymers,
d) modified or unmodified carboxyvinyl polymers,
e) mixtures thereof.

a) Water-Soluble Polysaccharides,

The term "polysaccharide" means any polymer consisting of several saccharides (or monosaccharides) having the general formula:

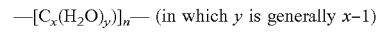

—[$C_x(H_2O)_y$)]$_n$— (in which $y$ is generally $x$–1)

and linked together via O-oside bonds.

The water-soluble polysaccharides that may be used in the present invention are especially chosen from starches, gellans, scleroglucan gum, guar gum, konjac, agar, and celluloses such as hydroxyethylcellulose and hydroxypropylcellulose, and mixtures thereof.

Starches are preferentially used.

The term "water-soluble" means partially or totally soluble in water to give a gelled or thickened solution at a concentration of 1% active material in water, after implementation with or without heating.

The starches that may be used in the present invention are more particularly macromolecules in the form of polymers formed from elemental units that are anhydroglucose units. The number of these units and their assembly make it possible to distinguish amylose (linear polymer) and amylopectin (branched polymer). The relative proportions of amylose and of amylopectin, and their degree of polymerization, vary as a function of the botanical origin of the starches. The amylose/amylopectin weight ratio may range from 30/70 (corn) to 16/84 (rice). The molecular weight of the amylose is preferably up to 1 million by weight and that of the amylopectin is preferably from 100 to 500 million by weight.

The starch molecules used in the present invention may be unmodified or chemically or physically modified.

Their botanical origin may be cereals or tubers. Thus, the natural starches may be chosen from corn starch, rice starch, tapioca starch, cassava starch, barley starch, potato starch, wheat starch, sorghum starch, palm starch and pea starch.

Among the unmodified starches, mention may be made of unmodified corn starches (INCI name: *Zea mays* starch), for instance the products sold under the trade name Farmal CS®, in particular the commercial product Farmal CS 3650® from the company Corn Products International.

Mention may also be made of unmodified rice starches (INCI name: *Oryza sativa* (rice) starch), for instance the commercial product Remy DR I® sold by the company Beneo-Remy.

According to a particular form of the invention, starches used are modified by crosslinking with functional agents capable of reacting with the hydroxyl groups of the starch molecules, which will thus bond together (for example with glyceryl and/or phosphate groups).

Monostarch phosphates (of the type St-O—PO—(OX)$_2$), distarch phosphates (of the type St-O—PO—(OX)—O-St) or even tristarch phosphates (of the type St-O—PO—(O-St)$_2$) or mixtures thereof may especially be obtained by crosslinking with phosphorus compounds.

X especially denotes alkali metals (for example sodium or potassium), alkaline-earth metals (for example calcium or magnesium), ammonium salts, amine salts, for instance those of monoethanolamine, diethanolamine, triethanolamine, 3-amino-1,2-propanediol, or ammonium salts derived from basic amino acids such as lysine, arginine, sarcosine, ornithine or citrulline.

The phosphorus compounds may be, for example, sodium tripolyphosphate, sodium orthophosphate, phosphorus oxychloride or sodium trimetaphosphate.

Use will preferentially be made of distarch phosphates or of compounds rich in distarch phosphate, in particular the distarch phosphate hydroxypropyl ethers having the INCI name: Hydroxypropyl Starch Phosphate, for instance the products sold under the trade names Farinex VA70 C or FARMAL MS 689® from the company Avebe Stadex; the products sold under the trade names Structure BTC®, Structure HVS®, Structure XL® or Structure Zea® from National Starch (corn distarch phosphate).

Preferentially, the starch will be chosen from unmodified corn starches, unmodified rice starches and corn distarch phosphates, or mixtures thereof.

According to the invention, the water-soluble polysaccharide(s) may preferably represent from 0.5% to 6% by weight and more particularly from 1% to 4% by weight relative to the total weight of the final composition.

b) Associative Polymers

For the purposes of the present invention, the term "associative polymers" means hydrophilic polymers that are capable, in an aqueous medium, of reversibly associating with each other or with other molecules. Their chemical structure more particularly comprises at least one hydrophilic region and at least one hydrophobic region.

The term "hydrophobic group" is understood to mean a radical or polymer containing a saturated or unsaturated and linear or branched hydrocarbon-based chain. When the hydrophobic group denotes a hydrocarbon-based radical, it comprises at least 10 carbon atoms, preferably from 10 to 30 carbon atoms, in particular from 12 to 30 carbon atoms and more preferentially from 18 to 30 carbon atoms.

Preferentially, the hydrocarbon-based group is derived from a monofunctional compound.

By way of example, the hydrophobic group may be derived from a fatty alcohol, such as stearyl alcohol, dodecyl alcohol or decyl alcohol, or else from a polyoxyalkylenated fatty alcohol, such as steareth-100. It may also denote a hydrocarbon-based polymer, for instance polybutadiene.

The associative polymers in accordance with the present invention may be anionic, cationic, nonionic or amphoteric.

Anionic Associative Polymers

Among the associative anionic polymers that may be mentioned are those comprising at least one hydrophilic unit, and at least one fatty-chain allyl ether unit, more particularly those whose hydrophilic unit is formed by an unsaturated ethylenic anionic monomer, more particularly by a vinylcarboxylic acid and most particularly by an acrylic acid or a methacrylic acid or mixtures thereof, and whose fatty-chain allyl ether unit corresponds to the monomer of formula (I) below:

CH$_2$=C(R')CH$_2$OB$n$R    (I)

in which R' denotes H or CH$_3$, B denotes an ethyleneoxy radical, n is zero or denotes an integer ranging from 1 to 100, R denotes a hydrocarbon-based radical chosen from alkyl, arylalkyl, aryl, alkylaryl and cycloalkyl radicals, comprising from 8 to 30 carbon atoms, preferably 10 to 24 and even more particularly from 12 to 18 carbon atoms.

Anionic amphiphilic polymers of this type are described and prepared, according to an emulsion polymerization process, in patent EP-0 216 479.

Among the associative anionic polymers, it is possible, according to a preferred embodiment, to use copolymers comprising among their monomers an α,β-monoethylenically unsaturated carboxylic acid and an ester of an α,β-monoethylenically unsaturated carboxylic acid and of an oxyalkylenated fatty alcohol.

Preferentially, these compounds also comprise as monomer an ester of an α,β-monoethylenically unsaturated carboxylic acid and of a C$_1$-C$_4$ alcohol.

Examples of compounds of this type that may be mentioned include Aculyn 22 (sold by the company Röhm & Haas, which is a methacrylic acid/ethyl acrylate/oxyalkylenated stearyl methacrylate (comprising 20 OE units) terpolymer or Aculyn 28 (methacrylic acid/ethyl acrylate/oxyethylenated behenyl methacrylate (25 OE) terpolymer).

Mention may also be made of crosslinked or noncrosslinked amphiphilic copolymers consisting of:
a) 2-acrylamido-2-methylpropanesulfonic acid (AMPS®) units of formula (II) below:

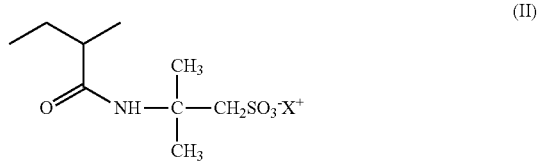

in which X is a proton, an alkali metal cation, an alkaline-earth metal cation or an ammonium ion; and
b) units of formula (III) below:

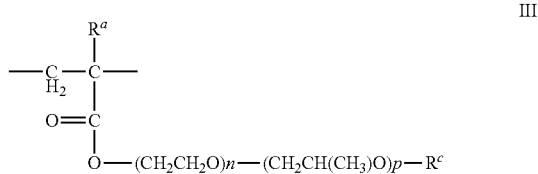

in which n and p, independently of each other, denote a number of moles and range from 0 to 30, preferably from 1 to 25 and more preferentially from 3 to 20, with the proviso that n+p is less than or equal to 30, preferably less than 25 and better still less than 20; R$^a$ denotes a hydrogen atom or a linear or branched C$_1$-C$_6$ alkyl radical, preferably methyl, and R$^c$ denotes a linear or branched alkyl comprising from 7 to 22 carbon atoms and preferably from 12 to 22 carbon atoms.

In formula (II), the cation X more particularly denotes sodium or ammonium.

Among the monomers of formula (III), mention may be made of:
  esters of (meth)acrylic acid and of a C$_{10}$-C$_{18}$ fatty alcohol polyoxyethylenated with 8 mol of ethylene oxide, for instance the product Genapol C-080® sold by the company Clariant,
  esters of (meth)acrylic acid and of a C$_{11}$ fatty oxoalcohol polyoxyethylenated with 8 mol of ethylene oxide, for instance the product Genapol UD-080® sold by the company Clariant,
  esters of (meth)acrylic acid and of a C$_{12}$-C$_{14}$ fatty alcohol polyoxyethylenated with 7 mol of ethylene oxide, for instance the product Genapol LA-070® sold by the company Clariant,
  esters of (meth)acrylic acid and of a C$_{12}$-C$_{14}$ fatty alcohol polyoxyethylenated with 11 mol of ethylene oxide, for instance the product Genapol LA-110® sold by the company Clariant, esters of (meth)acrylic acid and of a $C_{16}$-$C_{18}$ fatty alcohol polyoxyethylenated with 8 mol of ethylene oxide, for instance the product Genapol T-080® sold by the company Clariant, esters of (meth)acrylic acid and of a $C_{16}$-$C_{18}$ fatty alcohol polyoxyethylenated with mol of ethylene oxide EO, for instance the product Genapol T-150® sold by the company Clariant, esters of (meth)acrylic acid and of a $C_{16}$-$C_{18}$ fatty alcohol polyoxyethylenated with 11 mol of ethylene oxide, for instance the product Genapol T-110® sold by the company Clariant, esters of (meth)acrylic acid and of a $C_{16}$-$C_{18}$ fatty alcohol polyoxyethylenated with 20 mol of ethylene oxide, for instance the product Genapol T-200® sold by the company Clariant, esters of (meth)acrylic acid and of a $C_{16}$-$C_{18}$ fatty alcohol polyoxyethylenated with 25 mol of ethylene oxide, for instance the product Genapol T-250® sold by the company Clariant, esters of (meth)acrylic acid and of a $C_{18}$-$C_{22}$ fatty alcohol polyoxyethylenated with 25 mol of ethylene oxide and/or of a $C_{16}$-$C_{18}$ fatty isoalcohol polyoxyethylenated with 25 mol of ethylene oxide.

The products that will be chosen more particularly are:

the non-crosslinked products for which p=0, n=7 or 25, $R^a$ denotes a methyl and $R^c$ represents a mixture of $C_{12}$-$C_{14}$ or $C_{16}$-$C_{18}$ alkyl, the crosslinked products for which p=0, n=8 or 25, $R^a$ denotes a methyl and $R^c$ represents a mixture of $C_{16}$-$C_{18}$ alkyl.

These polymers are described and synthesized in patent application EP 1 069 142.

These particular amphiphilic AMPS® polymers may be obtained according to the standard free-radical polymerization processes in the presence of one or more initiators, for instance azobisisobutyronitrile (AIBN), azobisdimethylvaleronitrile, 2,2-azobis[2-amidinopropane]hydrochloride (ABAH=2,2-Azo-Bis-[2-Amidinopropane]Hydrochloride), organic peroxides such as dilauryl peroxide, benzoyl peroxide or tert-butyl hydroperoxide, mineral peroxide compounds such as potassium persulfate or ammonium persulfate, or $H_2O_2$ optionally in the presence of reducing agents.

These amphiphilic AMPS® polymers may be obtained especially by free-radical polymerization in tert-butanol medium, in which they precipitate. By using precipitation polymerization in tert-butanol, it is possible to obtain a size distribution of the polymer particles that is particularly favourable for its uses.

The reaction may be performed at a temperature of between 0 and 150° C. and preferably between 10 and 100° C., either at atmospheric pressure or under reduced pressure.

It may also be performed under inert atmosphere, and preferably under nitrogen.

The amphiphilic AMPS® polymers according to the invention may preferably be partially or totally neutralized with a mineral base such as sodium hydroxide, potassium hydroxide, aqueous ammonia or an organic base such as monoethanolamine, diethanolamine, triethanolamine, an aminomethylpropanediol, N-methylglucamine, basic amino acids, for instance arginine and lysine, and mixtures of these compounds. They may especially be totally or almost totally neutralized, i.e. at least 80% neutralized.

The molar percentage concentration of the units of formula (II) and of the units of formula (III) in the amphiphilic AMPS® polymers according to the invention may vary as a function of the desired cosmetic application, for example the nature of the emulsion (oil-in-water or water-in-oil emulsion) and the desired rheological properties of the formulation. It may range, for example, between 0.1 mol % and 99.9 mol %.

Preferably, for the most hydrophobic polymers, the molar proportion of units of formula (I) or (III) ranges from 50.1% to 99.9%, more particularly from 70% to 95% and even more particularly from 80% to 90%.

Preferably, for the sparingly hydrophobic polymers, the molar proportion of units of formula (I) or (III) ranges from 0.1% to 50%, more particularly from 5% to 25% and even more particularly from 10% to 20%.

The distribution of the monomers in the amphiphilic AMPS® polymers according to the invention may be, for example, alternate, block (including multiblock) or random.

As a guide, and without this being limiting, mention may be made especially of:

a non-crosslinked copolymer of 2-acrylamidomethylpropanesulfonic acid and of a $C_{12}$-$C_{14}$ alkyl methacrylate polyethoxylated with 25 mol of ethylene oxide (INCI name: Ammonium acryloyldimethyltaurate/laureth-7 methacrylate copolymer) (non-crosslinked copolymer obtained from Genapol LA-070 and AMPS®) sold under the name Aristoflex LNC by the company Clariant, a crosslinked copolymer of 2-acrylamidomethylpropanesulfonic acid and of stearyl methacrylate polyethoxylated with 25 mol of ethylene oxide (INCI name: Ammonium acryloyldimethyltaurate/steareth-25 methacrylate crosspolymer) (copolymer crosslinked with trimethylolpropane triacrylate obtained from Genapol T-250 and AMPS®) sold under the name Aristoflex HMS by the company Clariant, a non-crosslinked copolymer of 2-acrylamidomethylpropanesulfonic acid and of a $C_{16}/C_{18}$ alkyl methacrylate polyethoxylated with 8 mol of ethylene oxide (INCI name: Ammonium acryloyldimethyltaurate/steareth-8 methacrylate copolymer) sold under the name Aristoflex SNC by the company Clariant, a crosslinked copolymer of 2-acrylamidomethylpropanesulfonic acid and of behenyl methacrylate polyethoxylated with 25 mol of ethylene oxide, crosslinked with trimethylolpropane triacrylate (INCI name: Ammonium acryloyldimethyltaurate/beheneth-25 methacrylate crosspolymer) sold under the name Aristoflex HMB by the company Clariant, and mixtures thereof.

Examples of associative anionic polymers that may also be mentioned include anionic polymers comprising at least one hydrophilic unit of unsaturated olefinic carboxylic acid type, and at least one hydrophobic unit exclusively of the type such as a $(C_{10}$-$C_{30})$ alkyl ester of an unsaturated carboxylic acid. Examples that may be mentioned include the anionic polymers described and prepared according to U.S. Pat. Nos. 3,915,921 and 4,509,949.

Cationic Associative Polymers

Cationic associative polymers that may be mentioned include quaternized cellulose derivatives and polyacrylates bearing amine side groups.

The quaternized cellulose derivatives are, in particular:

quaternized celluloses modified with groups comprising at least one fatty chain, such as alkyl, arylalkyl or alkylaryl groups comprising at least 8 carbon atoms, or mixtures thereof, quaternized hydroxyethylcelluloses modified with groups comprising at least one fatty chain, such as alkyl, arylalkyl or alkylaryl groups comprising at least 8 carbon atoms, or mixtures thereof.

The polyacrylates bearing quaternized or non-quaternized amine side groups contain, for example, hydrophobic groups of the type such as steareth-20 (polyoxyethylenated (20) stearyl alcohol).

The alkyl radicals borne by the above quaternized celluloses or hydroxyethylcelluloses preferably comprise from 8 to 30 carbon atoms.

The aryl radicals preferably denote phenyl, benzyl, naphthyl or anthryl groups.

Examples of quaternized alkylhydroxyethylcelluloses containing $C_8$-$C_{30}$ fatty chains that may be indicated include the products Quatrisoft LM 200, Quatrisoft LM-X 529-18-A, Quatrisoft LM-X 529-18B ($C_{12}$ alkyl) and Quatrisoft LM-X 529-8 ($C_{18}$ alkyl) sold by the company Amerchol and the products Crodacel QM, Crodacel QL ($C_{12}$ alkyl) and Crodacel QS ($C_{18}$ alkyl) sold by the company Croda.

Examples of polyacrylates bearing amino side chains that may be mentioned are the polymers 8781-121 B or 9492-103 from the company National Starch.

Nonionic Associative Polymers

The nonionic associative polymers may be chosen from:
- celluloses modified with groups comprising at least one fatty chain, for instance hydroxyethylcelluloses modified with groups comprising at least one fatty chain, such as alkyl groups, especially of $C_8$-$C_{22}$, arylalkyl and alkylaryl groups, such as Natrosol Plus Grade 330 CS ($C_{16}$ alkyls) sold by the company Aqualon,
- celluloses modified with alkylphenol polyalkylene glycol ether groups, such as the product Amercell Polymer HM-1500 (nonylphenol polyethylene glycol (15) ether) sold by the company Amerchol,
- guars such as hydroxypropyl guar, modified with groups comprising at least one fatty chain such as an alkyl chain,
- inulins modified with groups comprising at least one fatty chain, such as alkyl carbamate inulins and in particular the lauryl carbamate inulin sold by the company Orafti under the name Inutec SP1 (see also page 9),
- diesters of polyethylene glycol and of a fatty acid, such as polyethylene glycol (150 OE) distearate, for instance PEG-150 Distearate sold under the trade name Emcol L 32-45® by Witco,
- associative polyurethanes.

Associative polyurethanes are nonionic block copolymers comprising in the chain both hydrophilic blocks usually of polyoxyethylene nature (polyurethanes may then be referred to as polyurethane polyethers), and hydrophobic blocks that may be aliphatic sequences alone and/or cycloaliphatic and/or aromatic sequences.

In particular, these polymers comprise at least two hydrocarbon-based lipophilic chains containing from 6 to 30 carbon atoms, separated by a hydrophilic block, the hydrocarbon-based chains possibly being pendent chains or chains at the end of the hydrophilic block. In particular, it is possible for one or more pendent chains to be provided. In addition, the polymer may comprise a hydrocarbon-based chain at one end or at both ends of a hydrophilic block.

Associative polyurethanes may be block polymers, in triblock or multiblock form. The hydrophobic blocks may thus be at each end of the chain (for example: triblock copolymer containing a hydrophilic central block) or distributed both at the ends and in the chain (for example: multiblock copolymer). These polymers may also be graft polymers or star polymers. Preferably, the associative polyurethanes are triblock copolymers in which the hydrophilic block is a polyoxyethylene chain comprising from 50 to 1000 oxyethylene groups. In general, associative polyurethanes comprise a urethane bond between the hydrophilic blocks, whence arises the name.

According to a preferred embodiment, a nonionic associative polymer of nonionic polyurethane polyether type is used as gelling agent.

As examples of nonionic fatty-chain polyurethane polyethers that may be used in the invention, it is also possible to use Rheolate® FX 1100 (steareth-100/PEG 136/HDI (hexamethyl diisocyanate) copolymer), Rheolate® 205® containing a urea function, sold by the company Elementis, or Rheolate® 208, 204 or 212, and also Acrysol RM 184® or Acrysol RM 2020.

Mention may also be made of the product Elfacos T210® containing a $C_{12}$-$C_{14}$ alkyl chain, and the product Elfacos T212® containing a $C_{16\text{-}18}$ alkyl chain (PPG-14 Palmeth-60 Hexyl Dicarbamate), from Akzo.

The product DW 1206B® from Röhm & Haas containing a $C_{20}$ alkyl chain and a urethane bond, sold at a solids content of 20% in water, may also be used.

It is also possible to use solutions or dispersions of these polymers, in particular in water or in aqueous-alcoholic medium. Examples of such polymers that may be mentioned are Rheolate® 255, Rheolate® 278 and Rheolate® 244 sold by the company Elementis. The products DW 1206F and DW 1206J sold by the company Röhm & Haas may also be used.

The associative polyurethanes that may be used according to the invention are in particular those described in the article by G. Fonnum, J. Bakke and Fk. Hansen—Colloid Polym. Sci., 271, 380-389 (1993).

Even more particularly, according to the invention, use may also be made of an associative polyurethane that may be obtained by polycondensation of at least three compounds comprising (i) at least one polyethylene glycol comprising from 150 to 180 mol of ethylene oxide, (ii) stearyl alcohol or decyl alcohol, and (iii) at least one diisocyanate.

Such polyurethane polyethers are sold especially by the company Röhm & Haas under the names Aculyn 46® and Aculyn 44® [Aculyn 46® is a polycondensate of polyethylene glycol containing 150 or 180 mol of ethylene oxide, of stearyl alcohol and of methylenebis(4-cyclohexyl isocyanate) (SMDI), at 15% by weight in a matrix of maltodextrin (4%) and water (81%); Aculyn 44® is a polycondensate of polyethylene glycol containing 150 or 180 mol of ethylene oxide, of decyl alcohol and of methylenebis(4-cyclohexyl isocyanate) (SMDI), at 35% by weight in a mixture of propylene glycol (39%) and water (26%)].

Use may also be made of solutions or dispersions of these polymers, in particular in water or in aqueous-alcoholic medium. Examples of such polymers that may be mentioned include Rheolate FX1010®, Rheolate FX1035® and Rheolate 1070® from the company Elementis, and Rheolate 255®, Rheolate 278® and Rheolate 244® sold by the company Elementis. Use may also be made of the products Aculyn 44, Aculyn 46®, DW 1206F® and DW 1206J®, and also Acrysol RM 184 from the company Röhm & Haas, or alternatively Borchi gel LW 44® from the company Borchers, and mixtures thereof.

Use will be made more particularly of an associative nonionic polyurethane polyether such as the product sold especially by the company Elementis under the name Rheolate FX1100®, which is a polycondensate of polyethylene glycol containing 136 mol of ethylene oxide, of stearyl alcohol polyoxyethylenated with 100 mol of ethylene oxide and of hexamethylene diisocyanate (HDI) with a weight-average molecular weight of 30 000 (INCI name: PEG-136/steareth-100l/SMDI Copolymer).

Amphoteric Associative Polymers

Among the associative amphoteric polymers of the invention, mention may be made of crosslinked or non-crosslinked, branched or unbranched amphoteric polymers, which may be obtained by copolymerization
1) of at least one monomer of formula (IVa) or (IVb):

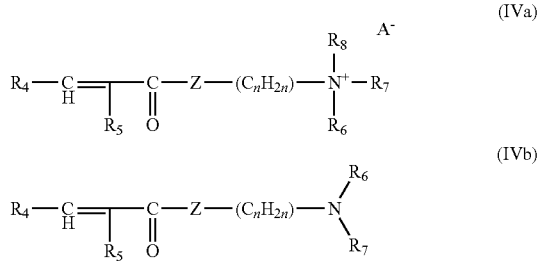

in which $R_4$ and $R_5$, which may be identical or different, represent a hydrogen atom or a methyl radical,
$R_6$, $R_7$ and $R_8$, which may be identical or different, represent a linear or branched alkyl radical containing from 1 to 30 carbon atoms,
Z represents a group NH or an oxygen atom,
n is an integer from 2 to 5,
A- is an anion derived from a mineral or organic acid, such as a methosulfate anion or a halide such as chloride or bromide,

in which $R_9$ and $R_{10}$, which may be identical or different, represent a hydrogen atom or a methyl radical;
$Z_1$ represents a group OH or a group $NHC(CH_3)_2CH_2SO_3H$;
3) of at least one monomer of formula (VI):

in which $R_9$ and $R_{10}$, which may be identical or different, represent a hydrogen atom or a methyl radical, X denotes an oxygen or nitrogen atom and $R_{11}$ denotes a linear or branched alkyl radical containing from 1 to 30 carbon atoms;
4) optionally at least one crosslinking or branching agent; at least one of the monomers of formula (IVa), (IVb) or (VI) comprising at least one fatty chain containing from 8 to 30 carbon atoms and the said compounds of the monomers of formulae (IVa), (IVb), (V) and (VI) possibly being quaternized, for example with a $C_1$-$C_4$ alkyl halide or a $C_1$-$C_4$ dialkyl sulfate.

The monomers of formulae (IVa) and (IVb) of the present invention are preferably chosen from the group formed by:
dimethylaminoethyl methacrylate, dimethylaminoethyl acrylate,
diethylaminoethyl methacrylate, diethylaminoethyl acrylate,
dimethylaminopropyl methacrylate, dimethylaminopropyl acrylate,
dimethylaminopropylmethacrylamide or dimethylaminopropylacrylamide, optionally quaternized, for example with a $C_1$-$C_4$ alkyl halide or a $C_1$-$C_4$ dialkyl sulfate.

More particularly, the monomer of formula (IVa) is chosen from acrylamidopropyltrimethylammonium chloride and methacrylamidopropyltrimethylammonium chloride.

The compounds of formula (V) of the present invention are preferably chosen from the group formed by acrylic acid, methacrylic acid, crotonic acid, 2-methylcrotonic acid, 2-acrylamido-2-methylpropanesulfonic acid and 2-methacrylamido-2-methylpropanesulfonic acid. More particularly, the monomer of formula (V) is acrylic acid.

The monomers of formula (VI) of the present invention are preferably chosen from the group formed by $C_{12}$-$C_{22}$ and more particularly $C_{16}$-$C_{18}$ alkyl acrylates or methacrylates.

The crosslinking or branching agent is preferably chosen from N,N'-methylenebisacrylamide, triallylmethylammonium chloride, allyl methacrylate, n-methylolacrylamide, polyethylene glycol dimethacrylates, ethylene glycol dimethacrylate, diethylene glycol dimethacrylate, 1,6-hexanediol dimethacrylate and allyl sucrose.

The polymers according to the invention may also contain other monomers such as nonionic monomers and in particular $C_1$-$C_4$ alkyl acrylates or methacrylates.

The ratio of the number of cationic charges/anionic charges in these amphoteric polymers is preferably equal to about 1.

The weight-average molecular weights of the associative amphoteric polymers have a weight-average molecular mass of greater than 500, preferably between 10 000 and 10 000 000 and even more preferentially between 100 000 and 8 000 000.

Preferably, the associative amphoteric polymers of the invention contain from 1 mol % to 99 mol %, more preferentially from 20 mol % to 95 mol % and even more preferentially from 25 mol % to 75 mol % of compound(s) of formula (IVa) or (IVb). They also preferably contain from 1 mol % to 80 mol %, more preferentially from 5 mol % to 80 mol % and even more preferentially from 25 mol % to 75 mol % of compound(s) of formula (V). The content of compound(s) of formula (VI) is preferably between 0.1 mol % and 70 mol %, more preferentially between 1 mol % and 50 mol % and even more preferentially between 1 mol % and 10 mol %. The crosslinking or branching agent, when it is present, is preferably between 0.0001 mol % and 1 mol % and even more preferentially between 0.0001 mol % and 0.1 mol %.

Preferably, the mole ratio between the compound(s) of formula (IVa) or (IVb) and the compound(s) of formula (V) ranges from 20/80 to 95/5 and more preferentially from 25/75 to 75/25.

The associative amphoteric polymers according to the invention are described, for example, in patent application WO 98/44012.

The amphoteric polymers that are particularly preferred according to the invention are chosen from acrylic acid/acrylamidopropyltrimethylammonium chloride/stearyl methacrylate copolymers.

The amount of associative nonionic polymer(s) as active material may range, for example, from 0.1% to 10% by weight, preferably from 0.25% to 6% by weight and better still from 0.5% to 3% by weight relative to the total weight of the composition.

c) Non-Associative, Crosslinked and/or Neutralized 2-Acrylamido-2-Methylpropanesulfonic Acid Polymers and Copolymers The polymers used that are suitable as aqueous gelling agent for the invention are crosslinked or non-crosslinked homopolymers or copolymers comprising at least the 2-acrylamidomethylpropanesulfonic acid (AMPS®) monomer, in a form partially or totally neutralized with a mineral base other than aqueous ammonia, such as sodium hydroxide or potassium hydroxide.

They are preferably totally or almost totally neutralized, i.e. at least 90% neutralized.

These AMPS® polymers according to the invention may be crosslinked or non-crosslinked.

When the polymers are crosslinked, the crosslinking agents may be chosen from the polyolefinically unsaturated compounds commonly used for crosslinking polymers obtained by free-radical polymerization.

Examples of crosslinking agents that may be mentioned include divinylbenzene, diallyl ether, dipropylene glycol diallyl ether, polyglycol diallyl ethers, triethylene glycol divinyl ether, hydroquinone diallyl ether, ethylene glycol or tetraethylene glycol di(meth)acrylate, trimethylolpropane triacrylate, methylenebisacrylamide, methylenebismethacrylamide, triallylamine, triallyl cyanurate, diallyl maleate, tetraallylethylenediamine, tetraallyloxyethane, trimethylolpropane diallyl ether, allyl (meth)acrylate, allylic ethers of alcohols of the sugar series, or other allyl or vinyl ethers of polyfunctional alcohols, and also the allylic esters of phosphoric and/or vinylphosphonic acid derivatives, or mixtures of these compounds.

According to one preferred embodiment of the invention, the crosslinking agent is chosen from methylenebisacrylamide, allyl methacrylate and trimethylolpropane triacrylate (TMPTA). The degree of crosslinking generally ranges from 0.01 mol % to 10 mol % and more particularly from 0.2 mol % to 2 mol % relative to the polymer.

The AMPS® polymers that are suitable for use in the invention are water-soluble or water-dispersible. They are in this case:
  either "homopolymers" comprising only AMPS monomers and, if they are crosslinked, one or more crosslinking agents such as those defined above;
  or copolymers obtained from AMPS® and from one or more ethylenically unsaturated monomers and, if they are crosslinked, one or more crosslinking agents such as those defined above.

The "homopolymers" according to the invention are preferably crosslinked and neutralized, and they may be obtained according to the preparation process comprising the following steps:
(a) the monomer such as AMPS in free form is dispersed or dissolved in a solution of tert-butanol or of water and tert-butanol;
(b) the monomer solution or dispersion obtained in (a) is neutralized with one or more mineral or organic bases, preferably aqueous ammonia NH3, in the amount making it possible to obtain a degree of neutralization of the sulfonic acid functions of the polymer ranging from 90% to 100%;
(c) the crosslinking monomer(s) are added to the solution or dispersion obtained in (b);
(d) a standard free-radical polymerization is performed in the presence of free-radical initiators at a temperature ranging from 10 to 150° C.; the polymer precipitates in the tert-butanol-based solution or dispersion.

The water-soluble or water-dispersible AMPS® copolymers according to the invention contain water-soluble ethylenically unsaturated monomers, hydrophobic monomers, or mixtures thereof.

The water-soluble co-monomers may be ionic or nonionic.

Among the ionic water-soluble co-monomers, mention may be made, for example, of the following compounds and salts thereof:
  (meth)acrylic acid,
  styrenesulfonic acid,
  vinylsulfonic acid and (meth)allylsulfonic acid,
  vinylphosphonic acid,
  maleic acid,
  itaconic acid,
  crotonic acid,
  water-soluble vinyl monomers of formula (A) below:

in which:
  $R^4$ is chosen from H, —$CH_3$, —$C_2H_5$ and —$C_3H_7$,
  $X_1$ is chosen from:
    alkyl oxides of type —$OR^5$ where $R^5$ is a linear or branched, saturated or unsaturated hydrocarbon-based radical containing from 1 to 6 carbon atoms, substituted with at least one sulfonic (—$SO_3$—) and/or sulfate (—$SO_4$—) and/or phosphate (—$PO_4H_2$—) group.

Among the nonionic water-soluble comonomers, mention may be made, for example, of:
  (meth)acrylamide,
  N-vinylacetamide and N-methyl-N-vinylacetamide,
  N-vinylformamide and N-methyl-N-vinylformamide,
  maleic anhydride,
  vinylamine,
  N-vinyllactams comprising a cyclic alkyl group containing from 4 to 9 carbon atoms, such as N-vinylpyrrolidone, N-butyrolactam and N-vinylcaprolactam,
  vinyl alcohol of formula $CH_2$=CHOH,
  water-soluble vinyl monomers of formula (B) below:

in which:
  $R^6$ is chosen from H, —$CH_3$, —$C_2H_5$ and —$C_3H_7$,
  $X_2$ is chosen from:
    alkyl oxides of the type —$OR^7$ where $R^7$ is a linear or branched, saturated or unsaturated hydrocarbon-based radical containing from 1 to 6 carbon atoms, optionally substituted with a halogen (iodine, bromine, chlorine or fluorine) atom; a hydroxyl (—OH) group; ether.

Mention may be made, for example, of glycidyl (meth) acrylate, hydroxyethyl methacrylate, and (meth)acrylates of ethylene glycol, of diethylene glycol or of polyalkylene glycol.

Among the hydrophobic co-monomers without a fatty chain, mention may be made, for example, of:

styrene and derivatives thereof, such as 4-butylstyrene, α-methylstyrene and vinyltoluene, vinyl acetate of formula $CH_2\!=\!CH\!-\!OCOCH_3$, vinyl ethers of formula $CH_2\!=\!CHOR^8$ in which $R^8$ is a linear or branched, saturated or unsaturated hydrocarbon-based radical containing from 1 to 6 carbon atoms, acrylonitrile, caprolactone, vinyl chloride and vinylidene chloride, silicone derivatives, which, after polymerization, result in silicone polymers such as methacryloxypropyltris(trimethylsiloxy)silane and silicone methacrylamides, hydrophobic vinyl monomers of formula (C) below:

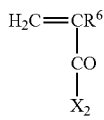

(B)

in which:

$R^9$ is chosen from H, $-CH_3$, $-C_2H_5$ and $-C_3H_7$, $X_3$ is chosen from:

alkyl oxides of the type $-OR^{10}$ where $R^{10}$ is a linear or branched, saturated or unsaturated hydrocarbon-based radical containing from 1 to 6 carbon atoms.

Mention may, for example, be made of methyl methacrylate, ethyl methacrylate, n-butyl (meth)acrylate, tert-butyl (meth)acrylate, cyclohexyl acrylate, isobornyl acrylate and 2-ethylhexyl acrylate.

The water-soluble or water-dispersible AMPS® polymers of the invention preferably have a molar mass ranging from 50 000 g/mol to 10 000 000 g/mol, preferably from 80 000 g/mol to 8 000 000 g/mol, and even more preferably from 100 000 g/mol to 7 000 000 g/mol.

As water-soluble or water-dispersible AMPS homopolymers suitable for use in the invention, mention may be made, for example, of crosslinked or non-crosslinked polymers of sodium acrylamido-2-methylpropanesulfonate, such as that used in the commercial product SIMULGEL 800 (CTFA name: Sodium Polyacryloyldimethyl Taurate), crosslinked ammonium acrylamido-2-methylpropanesulfonate polymers (INCI name: Ammonium polydimethyltauramide) such as those described in patent EP 0 815 928 B1 and such as the product sold under the trade name Hostacerin AMPS® by the company Clariant.

As water-soluble or water-dispersible AMPS copolymers in accordance with the invention, examples that may be mentioned include crosslinked acrylamide/sodium acrylamido-2-methylpropanesulfonate copolymers such that normally they do not comprise any AMPS units, this is a pure acrylamide that used in the commercial product sold under the trade name Simulgel 600 (CTFA name: Acrylamide/Sodium Acryloyldimethyltaurate/Isohexadecane/Polysorbate-80) by the company SEPPIC;

copolymers of AMPS® and of vinylpyrrolidone or vinylformamide, such as that used in the commercial product sold under the name Aristoflex AVC® by the company Clariant (CTFA name: Ammonium acryloyldimethyltaurate/VP copolymer) but neutralized with sodium hydroxide or potassium hydroxide;

copolymers of AMPS® and of sodium acrylate, for instance the AMPS/sodium acrylate copolymer, such as that used in the commercial product sold under the name Simulgel EG® by the company SEPPIC or under the trade name Sepinov EM (CTFA name: Hydroxyethyl acrylate/sodium acryloyldimethyl taurate copolymer)

copolymers of AMPS® and of hydroxyethyl acrylate, for instance the AMPS®/hydroxyethyl acrylate copolymer, such as that used in the commercial product sold under the name Simulgel NS® by the company SEPPIC (CTFA name: Hydroxyethyl acrylate/sodium acryloyldimethyltaurate copolymer (and) squalane (and) polysorbate 60, or such as the product sold under the name Sodium acrylamido-2-methylpropanesulfonate/hydroxyethyl acrylate copolymer, such as the commercial product Sepinov EMT 10 (INCI name: Hydroxyethyl acrylate/sodium acryloyldimethyl taurate copolymer).

d) Modified or Unmodified Carboxyvinyl Polymers

Among the modified or unmodified carboxyvinyl polymers, mention may be made of carboxyvinyl polymers, crosslinked polyacrylic acids, such as carbomers such as Carbopols® and acrylate/$C_{10}$-$C_{30}$ alkyl acrylate crosslinked copolymers such as Pemulen TR1® and Pemulen TR2®.=>idem should be in the anionic associative products?

Among the hydrophilic structuring agents, use will be made more particularly of:

nonionic associative polymers and more particularly nonionic associative urethane polyethers, even more particularly a polycondensate of polyethylene glycol containing 136 mol of ethylene oxide, of stearyl alcohol polyoxyethylenated with 100 mol of ethylene oxide and of hexamethylene diisocyanate (HDI) with a weight-average molecular weight of 30 000 (INCI name: PEG-136/steareth-100l/SMDI Copolymer).

starches, and mixtures thereof.

B) Lipophilic Structuring Agents

Among the lipophilic structuring agents that may be used according to the invention, mention may be made of:

a) waxes, b) hydrophobic-modified clays, c) hydrophobic-modified silicas, d) silicone elastomers, and mixtures thereof.

a) Waxes

The term "wax" under consideration in the context of the present invention generally means a lipophilic compound that is solid at room temperature (25° C.), with a solid/liquid reversible change of state, having a melting point of greater than or equal to 45° C., which may be up to 200° C. and in particular up to 120° C.

For the purposes of the invention, the melting point corresponds to the temperature of the most endothermic peak observed on thermal analysis (DSC) as described in standard ISO 11357-3; 1999. The melting point of the surfactant or of the wax can be measured using a differential scanning calorimeter (DSC), for example the calorimeter sold under the name MDSC 2920 by TA Instruments.

The Measurement Protocol is as Follows:

A sample of 5 mg of surfactant placed in a crucible is subjected to a first temperature rise ranging from −20° C. to 100° C., at a heating rate of 10° C./minute, it is then cooled from 100° C. to −20° C. at a cooling rate of 10° C./minute and is finally subjected to a second temperature increase ranging from −20° C. to 100° C. at a heating rate of 5° C./minute. During the second temperature rise, the variation in the difference between the power absorbed by the empty crucible and the crucible containing the sample of surfactant or wax as a function of the temperature is measured. The melting point of the compound is the temperature value corresponding to the top of the peak of the curve representing the variation in the difference in power absorbed as a function of the temperature.

The waxes that may be used in the compositions according to the invention are preferably chosen from waxes with a melting point of greater than 45° C. comprising one or more $C_{40}$-$C_{70}$ ester compounds and not comprising any $C_{20}$-$C_{39}$ ester compounds.

The term "ester compound" means any organic molecule comprising a linear or branched, saturated or unsaturated hydrocarbon-based chain comprising at least one ester function of formula —COOR in which R represents a hydrocarbon-based radical, in particular a saturated linear alkyl radical.

The term "wax not comprising any $C_{20}$-$C_{39}$ ester compounds" means any wax containing less than 1% by weight and preferably less than 0.5% by weight of $C_{20}$-$C_{39}$ ester compounds relative to the weight of the wax, or even being free of $C_{20}$-$C_{39}$ ester compounds.

The waxes according to the invention may also be used in the form of a mixture of waxes.

The content of ester comprising from 20 to 70 carbon atoms and preferably from 40 to 70 carbon atoms preferably ranges from 20% to 100% by weight and preferably from 20% to 90% by weight relative to the total weight of wax(es).

As illustrations of the waxes that are suitable for use in the invention, mention may be made especially of hydrocarbon-based waxes such as candelilla wax, rice bran wax, beeswax and sunflower wax, and mixtures thereof.

Use will be made more particularly of candelilla wax and/or beeswax.

The composition according to the invention may comprise a wax content preferably ranging from 1% to 10% by weight and in particular from 2% to 8% by weight relative to the total weight of the composition.

b) Hydrophobic-Modified Clays

Among the hydrophobic-modified clays that may be used according to the invention, mention may be made of hydrophobic-modified montmorillonite clays such as hydrophobic-modified bentonites or hectorites. Examples that may be mentioned include the product Stearalkonium Bentonite (CTFA name) (product of reaction of bentonite and the quaternary ammonium stearalkonium chloride) such as the commercial product sold under the name Tixogel MP 250 by the company Sud Chemie Rheologicals, United Catalysts Inc. or the product Disteardimonium Hectorite (CTFA name) (product of reaction of hectorite and distearyldimonium chloride) sold under the name Bentone 38 or Bentone Gel by the company Elementis Specialities.

c) Hydrophobic-Modified Silicas

The hydrophobic-modified silicas that may be used according to the invention may be chosen especially from:
i) hydrophobic-modified fumed silicas,
ii) hydrophobic silica aerogels,
iii) mixtures thereof.

i) Hydrophobic-Modified Fumed Silicas

Fumed silica subjected to a hydrophobic surface treatment, the particle size of which is less than 1 µm, is most particularly suitable for use in the invention. Specifically, it is possible to chemically modify the surface of silica, via a chemical reaction that generates a reduction in the number of silanol groups present at the surface of the silica. Silanol groups can in particular be replaced by hydrophobic groups: a hydrophobic silica is then obtained.

The hydrophobic groups may be:
trimethylsiloxyl groups, which are obtained in particular by treating fumed silica in the presence of hexamethyldisilazane.

Silicas thus treated are named "Silica silylate" according to the CTFA (8th edition, 2000). They are sold, for example, under the references Aerosil R812® by the company Degussa, and Cab-O-Sil TS-530® by the company Cabot;
dimethylsilyloxyl or polydimethylsiloxane groups, which are obtained in particular by treating fumed silica in the presence of polydimethylsiloxane or dimethyldichlorosilane.

Silicas thus treated are named "Silica dimethyl silylate" according to the CTFA (8th edition, 2000). They are, for example, sold under the references Aerosil R972® and Aerosil R974® by the company Degussa and Cab-O-Sil TS-610® and Cab-O-Sil TS-720® by the company Cabot.

ii) Hydrophobic Silica Aerogels

Silica aerogels are porous materials obtained by replacing (by drying) the liquid component of a silica gel with air.

They are generally synthesized via a sol-gel process in a liquid medium and then dried, usually by extraction with a supercritical fluid, the one most commonly used being supercritical $CO_2$. This type of drying makes it possible to avoid the contraction of the pores and of the material. The sol-gel process and the various drying operations are described in detail in Brinker C. J. and Scherer G. W., Sol-Gel Science, New York: Academic Press, 1990.

The hydrophobic silica aerogel particles used in the present invention have a specific surface area per unit of mass (SM) ranging from 500 to 1500 $m^2$/g, preferably from 600 to 1200 $m^2$/g and better still from 600 to 800 $m^2$/g, and a size expressed as the volume-mean diameter (D[0.5]) ranging from 1 to 1500 µm, better still from 1 to 1000 µm, preferably from 1 to 100 µm, in particular from 1 to 30 µm, more preferably from 5 to 25 µm, better still from 5 to 20 µm and even better still from 5 to 15 µm.

According to one embodiment, the hydrophobic silica aerogel particles used in the present invention have a size expressed as volume-mean diameter (D[0.5]) ranging from 1 to 30 µm, preferably from 5 to 25 µm, better still from 5 to 20 µm and even better still from 5 to 15 µm.

The specific surface area per unit of mass can be determined by the nitrogen absorption method, known as the BET (Brunauer-Emmett-Teller) method, described in the Journal of the American Chemical Society, Vol. 60, page 309, February 1938, which corresponds to international standard ISO 5794/1 (appendix D). The BET specific surface area corresponds to the total specific surface area of the particles under consideration.

The sizes of the silica aerogel particles may be measured by static light scattering using a commercial particle size analyser such as the MasterSizer 2000 machine from Malvern. The data are processed on the basis of the Mie scattering theory. This theory, which is exact for isotropic particles, makes it possible to determine, in the case of non-spherical particles, an "effective" particle diameter. This theory is described in particular in the publication by Van de Hulst, N. C., "Light Scattering by Small Particles", Chapters 9 and 10, Wiley, New York, 1957.

According to an advantageous embodiment, the hydrophobic silica aerogel particles used in the present invention have a specific surface area per unit of mass (SM) ranging from 600 to 800 $m^2$/g and a size expressed as the volume-mean diameter (D[0.5]) ranging from 5 to 20 µm and even better still from 5 to 15 µm.

The silica aerogel particles used in the present invention may advantageously have a tapped density r ranging from 0.02 g/cm$^3$ to 0.10 g/cm$^3$, preferably from 0.03 g/cm$^3$ to 0.08 g/cm$^3$ and in particular ranging from 0.05 g/cm$^3$ to 0.08 g/cm$^3$.

In the context of the present invention, this density may be assessed according to the following protocol, known as the tapped density protocol:

40 g of powder are poured into a measuring cylinder; the measuring cylinder is then placed on a Stav 2003 machine from Stampf Volumeter; the measuring cylinder is then subjected to a series of 2500 packing motions (this operation is repeated until the difference in volume between two consecutive tests is less than 2%); the final volume Vf of tapped powder is then measured directly on the measuring cylinder. The tapped density is determined by the ratio w/Vf, in this instance 40/Vf (Vf being expressed in cm$^3$ and w in g).

According to a preferred embodiment, the hydrophobic silica aerogel particles used in the present invention have a specific surface area per unit of volume SV ranging from 5 to 60 m$^2$/cm$^3$, preferably from 10 to 50 m$^2$/cm$^3$ and better still from 15 to 40 m$^2$/cm$^3$.

The specific surface area per unit of volume is given by the relationship: SV=SM×r, where r is the tapped density, expressed in g/cm$^3$, and SM is the specific surface area per unit of mass, expressed in m$^2$/g, as defined above.

Preferably, the hydrophobic silica aerogel particles according to the invention have an oil-absorbing capacity, measured at the wet point, ranging from 5 to 18 ml/g, preferably from 6 to 15 ml/g and better still from 8 to 12 ml/g.

The absorption capacity measured at the wet point, denoted Wp, corresponds to the amount of oil which it is necessary to add to 100 g of particles in order to obtain a homogeneous paste.

It is measured according to the "wet point" method or method for determining the oil uptake of a powder described in standard NF T 30-022. It corresponds to the amount of oil adsorbed onto the available surface of the powder and/or absorbed by the powder by measuring the wet point, described below:

an amount m=2 g of powder is placed on a glass plate, and the oil (isononyl isononanoate) is then added dropwise. After addition of 4 to 5 drops of oil to the powder, mixing is performed using a spatula, and addition of oil is continued until a conglomerate of oil and powder has formed. From this point, the oil is added one drop at a time and the mixture is then triturated with the spatula. The addition of oil is stopped when a firm, smooth paste is obtained. This paste must be able to be spread over the glass plate without cracks or the formation of lumps. The volume Vs (expressed in ml) of oil used is then noted.

The oil uptake corresponds to the ratio Vs/m.

The aerogels used according to the present invention are aerogels of hydrophobic silica, preferably of silylated silica (INCI name: silica silylate).

The term "hydrophobic silica" means any silica whose surface is treated with silylating agents, for example halogenated silanes such as alkylchlorosilanes, siloxanes, in particular dimethylsiloxanes such as hexamethyldisiloxane, or silazanes, so as to functionalize the OH groups with silyl groups Si—Rn, for example trimethylsilyl groups.

As regards the preparation of hydrophobic silica aerogel particles that have been surface-modified by silylation, reference may be made to document U.S. Pat. No. 7,470,725.

Use will preferably be made of hydrophobic silica aerogel particles surface-modified with trimethylsilyl groups, preferably of the INCI name Silica silylate.

As hydrophobic silica aerogels that may be used in the invention, examples that may be mentioned include the aerogel sold under the name VM-2260 or VM-2270 (INCI name: Silica silylate), by the company Dow Corning, the particles of which have an average size of about 1000 microns and a specific surface area per unit of mass ranging from 600 to 800 m$^2$/g.

Mention may also be made of the aerogels sold by the company Cabot under the references Aerogel TLD 201, Aerogel OGD 201 and Aerogel TLD 203, Enova® Aerogel MT 1100 and Enova Aerogel MT 1200.

Use will preferably be made of the aerogel sold under the name VM-2270 (INCI name: Silica silylate), by the company Dow Corning, the particles of which have an average size ranging from 5-15 microns and a specific surface area per unit of mass ranging from 600 to 800 m$^2$/g.

Preferably, the hydrophobic silica aerogel particles are present in the composition according to the invention in an active material content ranging from 0.1% to 3% by weight, preferably from 0.2% to 2% by weight and preferably from 0.2% to 1% by weight relative to the total weight of the oily phase.

d) Silicone Elastomers

The term "organopolysiloxane elastomer" or "silicone elastomer" means a supple, deformable organopolysiloxane with viscoelastic properties and especially with the consistency of a sponge or a supple sphere. Its modulus of elasticity is such that this material withstands deformation and has a limited ability to extend and to contract. This material is capable of regaining its original shape after stretching.

It is more particularly a crosslinked organopolysiloxane elastomer.

Thus, the organopolysiloxane elastomer may be obtained by crosslinking addition reaction of diorganopolysiloxane containing at least one hydrogen bonded to silicon and of diorganopolysiloxane containing ethylenically unsaturated groups bonded to silicon, especially in the presence of a platinum catalyst; or by dehydrogenation crosslinking condensation reaction between a diorganopolysiloxane containing hydroxyl end groups and a diorganopolysiloxane containing at least one hydrogen bonded to silicon, especially in the presence of an organotin; or by crosslinking condensation reaction of a diorganopolysiloxane containing hydroxyl end groups and of a hydrolysable organopolysilane; or by thermal crosslinking of organopolysiloxane, especially in the presence of an organoperoxide catalyst; or by crosslinking of organopolysiloxane via high-energy radiation such as gamma rays, ultraviolet rays or an electron beam.

Preferably, the organopolysiloxane elastomer is obtained by crosslinking addition reaction (A) of diorganopolysiloxane containing at least two hydrogens each bonded to a silicon, and (B) of diorganopolysiloxane containing at least two ethylenically unsaturated groups bonded to silicon, especially in the presence (C) of a platinum catalyst, as described, for instance, in patent application EP-A-295 886.

In particular, the organopolysiloxane elastomer may be obtained by reaction of a dimethylpolysiloxane containing dimethylvinylsiloxy end groups and of methylhydrogenopolysiloxane containing trimethylsiloxy end groups, in the presence of a platinum catalyst.

Compound (A) is the base reagent for the formation of organopolysiloxane elastomer, and the crosslinking is performed by addition reaction of compound (A) with compound (B) in the presence of the catalyst (C).

Compound (A) is in particular an organopolysiloxane containing at least two hydrogen atoms bonded to different silicon atoms in each molecule.

Compound (A) can exhibit any molecular structure, in particular a linear chain or branched chain structure or a cyclic structure.

Compound (A) can have a viscosity at 25° C. ranging from 1 to 50 000 centistokes, in particular in order to be satisfactorily miscible with compound (B).

The organic groups bonded to the silicon atoms of compound (A) may be alkyl groups such as methyl, ethyl, propyl, butyl, octyl; substituted alkyl groups such as 2-phenylethyl, 2-phenylpropyl or 3,3,3-trifluoropropyl; aryl groups such as phenyl, tolyl, xylyl; substituted aryl groups such as phenylethyl; and substituted monovalent hydrocarbon-based groups such as an epoxy group, a carboxylate ester group or a mercapto group.

Compound (A) can thus be chosen from methylhydropolysiloxanes containing trimethylsiloxy end groups, dimethylsiloxane-methylhydrosiloxane copolymers containing trimethylsiloxy end groups, and dimethylsiloxane-methylhydrosiloxane cyclic copolymers.

Compound (B) is advantageously a diorganopolysiloxane containing at least two lower alkenyl groups (for example $C_2$-$C_4$); the lower alkenyl group may be chosen from vinyl, allyl and propenyl groups. These lower alkenyl groups can be located at any position on the organopolysiloxane molecule but are preferably located at the ends of the organopolysiloxane molecule. The organopolysiloxane (B) can have a branched-chain, linear-chain, cyclic or network structure but the linear-chain structure is preferred. The compound (B) can have a viscosity ranging from the liquid state to the gum state. Preferably, the compound (B) has a viscosity of at least 100 centistokes at 25° C.

Besides the abovementioned alkenyl groups, the other organic groups bonded to the silicon atoms in compound (B) may be alkyl groups such as methyl, ethyl, propyl, butyl or octyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group.

The organopolysiloxanes (B) can be chosen from methylvinylpolysiloxanes, methylvinylsiloxane-dimethylsiloxane copolymers, dimethylpolysiloxanes containing dimethylvinylsiloxy end groups, dimethylsiloxane-methylphenylsiloxane copolymers containing dimethylvinylsiloxy end groups, dimethylsiloxane-diphenylsiloxane-methylvinylsiloxane copolymers containing dimethylvinylsiloxy end groups, dimethylsiloxane-methylvinylsiloxane copolymers containing trimethylsiloxy end groups, dimethylsiloxane-methylphenylsiloxane-methylvinylsiloxane copolymers containing trimethylsiloxy end groups, methyl(3,3,3-trifluoropropyl)polysiloxanes containing dimethylvinylsiloxy end groups, and dimethylsiloxane-methyl(3,3,3-trifluoropropyl)siloxane copolymers containing dimethylvinylsiloxy end groups.

In particular, the organopolysiloxane elastomer may be obtained by reaction of dimethylpolysiloxane containing dimethylvinylsiloxy end groups and of methylhydrogenopolysiloxane containing trimethylsiloxy end groups, in the presence of a platinum catalyst.

Advantageously, the sum of the number of ethylene groups per molecule of compound (B) and of the number of hydrogen atoms bonded to silicon atoms per molecule of compound (A) is at least 5.

It is advantageous for compound (A) to be added in an amount such that the molecular ratio of the total amount of hydrogen atoms bonded to silicon atoms in compound (A) to the total amount of all the ethylenically unsaturated groups in compound (B) is within the range from 1.5/1 to 20/1.

Compound (C) is the catalyst of the crosslinking reaction and is in particular chloroplatinic acid, chloroplatinic acid/olefin complexes, chloroplatinic acid/alkenylsiloxane complexes, chloroplatinic acid/diketone complexes, platinum black and platinum-on-support.

The catalyst (C) is preferably added from 0.1 to 1000 parts by weight, better still from 1 to 100 parts by weight, as platinum metal proper, per 1000 parts by weight of the total amount of compounds (A) and (B).

The elastomer is advantageously a non-emulsifying elastomer.

The term "non-emulsifying" defines organopolysiloxane elastomers not containing any hydrophilic chains, and in particular not containing any polyoxyalkylene units (especially polyoxyethylene or polyoxypropylene) or any polyglyceryl units. Thus, according to one particular mode of the invention, the composition comprises an organopolysiloxane elastomer free of polyoxyalkylene units and of polyglyceryl units.

The organopolysiloxane elastomer particles are conveyed in the form of a gel formed from an elastomeric organopolysiloxane included in at least one hydrocarbon-based oil and/or one silicone oil. In these gels, the organopolysiloxane particles are often nonspherical particles.

Non-emulsifying elastomers are described especially in patents EP 242 219, EP 285 886 and EP 765 656 and in patent application JP-A-61-194009, the content of which is incorporated herein by way of reference. Non-emulsifying elastomers that may be used more particularly include those sold under the names KSG-6, KSG-15, KSG-16, KSG-18, KSG-41, KSG-42, KSG-43 and KSG-44 by the company Shin-Etsu, DC9040 and DC9041 by the company Dow Corning, and SFE 839 by the company General Electric.

Spherical non-emulsifying elastomers that may be used include those sold under the names DC 9040, DC 9041, DC 9509, DC 9505 and DC 9506 by the company Dow Corning.

Among the lipophilic structuring agents, use will be made more particularly of at least one wax as defined previously.

Aqueous Phase

The term "aqueous phase" means a phase comprising water and generally any molecule in dissolved form in the water in the composition.

The aqueous phase of the said compositions contains water and generally other water-soluble or water-miscible solvents. The water-soluble or water-miscible solvents comprise monoalcohols with a short chain, for example of $C_1$-$C_4$, such as ethanol or isopropanol; diols or polyols, for instance ethylene glycol, 1,2-propylene glycol, 1,3-butylene glycol, hexylene glycol, diethylene glycol, dipropylene glycol, 2-ethoxyethanol, diethylene glycol monomethyl ether, triethylene glycol monomethyl ether and sorbitol. Propylene glycol, glycerol and 1,3-propanediol will be used more particularly.

The concentration of the aqueous phase preferably ranges from 10% to 90% by weight and preferably from 30% to 90% by weight relative to the total weight of the composition.

The aqueous compositions of the invention may be in gel or cream form in the form of a simple or complex emulsion (O/W, W/O, O/W/O or W/O/W).

The emulsions generally contain at least one emulsifier chosen from amphoteric, anionic, cationic and nonionic emulsifiers, used alone or as a mixture. The emulsifiers are appropriately chosen according to the emulsion to be obtained (W/O or O/W).

Examples of W/O emulsifying surfactants that may be mentioned include alkyl esters or ethers of sorbitan, of glycerol, of polyol or of sugars; silicone surfactants, for instance dimethicone copolyols, such as the mixture of cyclomethicone and of dimethicone copolyol, sold under the name DC 5225 C® by the company Dow Corning, and alkyldimethicone copolyols such as laurylmethicone copolyol sold under the name Dow Corning 5200 Formulation Aid by the company Dow Corning; cetyldimethicone copolyol, such as the product sold under the name Abil EM 90R® by the company Goldschmidt, and the mixture of cetyldimethicone copolyol, of polyglyceryl isostearate (4 mol) and of hexyl laurate, sold under the name Abil WE O9® by the company Goldschmidt. One or more coemulsifiers may also be added thereto, which may be chosen advantageously from the group comprising polyol alkyl esters.

Mention may also be made of non-silicone emulsifying surfactants, in particular alkyl esters or ethers of sorbitan, of glycerol, of polyol or of sugars.

Polyol alkyl esters that may especially be mentioned include polyethylene glycol esters, for instance PEG-30 dipolyhydroxystearate, such as the product sold under the name Arlacel P135® by the company ICI.

Examples of glycerol and/or sorbitan esters that may be mentioned include polyglyceryl isostearate, such as the product sold under the name Isolan GI 34® by the company Goldschmidt; sorbitan isostearate, such as the product sold under the name Arlacel 987® by the company ICI; sorbitan glyceryl isostearate, such as the product sold under the name Arlacel 986® by the company ICI, and mixtures thereof.

For the O/W emulsions, examples of nonionic emulsifying surfactants that may be mentioned include polyoxyalkylenated (more particularly polyoxyethylenated and/or polyoxypropylenated) esters of fatty acids and of glycerol; oxyalkylenated esters of fatty acids and of sorbitan; polyoxyalkylenated (in particular polyoxyethylenated and/or polyoxypropylenated) esters of fatty acids, optionally in combination with an ester of fatty acid and of glycerol, such as the PEG-100 Stearate/Glyceryl Stearate mixture sold, for example, by the company ICI under the name Arlacel 165; oxyalkylenated (oxyethylenated and/or oxypropylenated) ethers of fatty alcohols; esters of sugars, such as sucrose stearate; or ethers of fatty alcohol and of sugar, in particular alkyl polyglucosides (APGs), such as decyl glucoside and lauryl glucoside, sold, for example, by the company Henkel under the respective names Plantaren 2000® and Plantaren 1200®, cetostearyl glucoside, optionally as a mixture with cetostearyl alcohol, sold, for example, under the name Montanov 68® by the company SEPPIC, under the name Tegocare CG90® by the company Goldschmidt and under the name Emulgade KE3302® by the company Henkel, and arachidyl glucoside, for example in the form of the mixture of arachidyl and behenyl alcohols and of arachidyl glucoside sold under the name Montanov 202® by the company SEPPIC. According to a particular embodiment of the invention, the mixture of the alkylpolyglucoside as defined above with the corresponding fatty alcohol may be in the form of a self-emulsifying composition, for example as described in document WO-A-92/06778.

According to a particular form of the invention, the composition is in the form of an oil-in-water emulsion.

Oily Phase

The compositions according to the invention contain at least one water-immiscible organic liquid phase, known as an oily phase. This phase generally comprises one or more hydrophobic compounds that make the said phase water-immiscible. The said phase is liquid (in the absence of structuring agent) at room temperature (20-25° C.).

Preferentially, the water-immiscible organic-liquid organic phase in accordance with the invention generally comprises at least one volatile or non-volatile hydrocarbon-based oil and optionally at least one volatile or non-volatile silicone oil.

The term "oil" means a fatty substance which is liquid at room temperature (25° C.) and atmospheric pressure (760 mmHg, i.e. $10^5$ Pa). The oil may be volatile or non-volatile.

For the purposes of the invention, the term "volatile oil" means an oil that is capable of evaporating on contact with the skin or the keratin fibre in less than one hour, at room temperature and atmospheric pressure. The volatile oils of the invention are volatile cosmetic oils which are liquid at room temperature and which have a non-zero vapour pressure, at room temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

The term "non-volatile oil" means an oil that remains on the skin or the keratin fibre at room temperature and atmospheric pressure for at least several hours, and that especially has a vapour pressure of less than $10^{-3}$ mmHg (0.13 Pa).

The oils in accordance with the invention are preferably chosen from any cosmetically acceptable oil, especially mineral, animal, plant or synthetic oils, especially hydrocarbon-based oils or silicone oils, or mixtures thereof.

The term "hydrocarbon-based oil" means an oil mainly comprising carbon and hydrogen atoms and possibly one or more functions chosen from hydroxyl, ester, ether and carboxylic functions. Generally, the oil has a viscosity of from 0.5 to 100 000 mPa·s and preferably from 50 to 50 000 mPa·s and more preferably from 100 to 30 000 mPa·s.

The term "silicone oil" means an oil comprising in its structure carbon atoms and at least one silicon atom.

As examples of volatile hydrocarbon-based oils that may be used in the invention, mention may be made of:

volatile hydrocarbon-based oils chosen from hydrocarbon-based oils containing from 8 to 16 carbon atoms, and in particular $C_8$-$C_{16}$ isoalkanes of petroleum origin (also known as isoparaffins), for instance isododecane (also known as 2,2,4,4,6-pentamethylheptane), isodecane and isohexadecane, for example the oils sold under the trade names Isopar or Permethyl, branched $C_8$-$C_{16}$ esters and isohexyl neopentanoate, and mixtures thereof. Use may also be made of other volatile hydrocarbon-based oils, such as petroleum distillates, in particular those sold under the name Shell Solt by the company Shell; and volatile linear alkanes, such as those described in patent application DE10 2008 012 457 from the company Cognis;

As examples of non-volatile hydrocarbon-based oils that may be used in the invention, mention may be made of:

vegetable hydrocarbon-based oils, such as liquid triglycerides of fatty acids containing 4 to 24 carbon atoms, such as heptanoic or octanoic acid triglycerides, or else wheat germ oil, olive oil, sweet almond oil, palm oil, rapeseed oil, cottonseed oil, alfalfa oil, poppy seed oil, pumpkin seed oil, cucumber oil, blackcurrant oil, evening primrose oil, millet oil, barley oil, quinoa oil, rye oil, safflower oil, candlenut oil, passionflower oil, musk rose oil, sunflower oil, maize oil, soybean oil, marrow oil, grape seed oil, sesame oil, hazelnut oil, apricot oil, macadamia oil, castor oil, avocado oil, caprylic/capric acid triglycerides, such as those sold by Stearineries Dubois or those sold under the names Miglyol 810, 812 and 818 by Dynamit Nobel, jojoba oil or shea butter oil;

synthetic ethers containing from 10 to 40 carbon atoms, such as dimethyl ether;

synthetic esters, especially of fatty acids, for instance the oils of formula $R_1COOR_2$ in which $R_1$ represents a linear or branched higher fatty acid residue comprising from 1 to 40 carbon atoms and $R_2$ represents a hydrocarbon-based chain, which is especially branched, containing from 1 to 40 carbon atoms, with $R_1+R_2 \geq 10$, for instance purcellin oil (cetostearyl octanoate), isononyl isononanoate, isopropyl myristate, isopropyl palmitate, $C_{12}$-$C_{15}$ alkyl benzoates, hexyl laurate, diisopropyl adipate, isononyl isononanoate, 2-ethylhexyl palmitate, 2-octyldodecyl stearate, 2-octyldodecyl erucate, isostearyl isostearate or tridecyl trimellitate; alcohol or polyalcohol octanoates, decanoates or ricinoleates, for instance propylene glycol dioctanoate; hydroxylated esters, for instance isostearyl lactate, octyl hydroxystearate, octyldodecyl hydroxystearate, diisostearyl malate, triisocetyl citrate, and fatty alcohol heptanoates, octanoates or decanoates; polyol esters, for instance propylene glycol dioctanoate, neopentyl glycol diheptanoate or diethylene glycol diisononanoate; and pentaerythritol esters, for instance pentaerythrityl tetra isostearate;

linear or branched hydrocarbons, of mineral or synthetic origin, such as liquid paraffins and derivatives thereof, petroleum jelly, polydecenes, polybutenes, hydrogenated polyisobutene such as Parleam, and squalane;

fatty alcohols which are liquid at room temperature and which comprise a branched and/or unsaturated carbon-based chain containing from 12 to 26 carbon atoms, such as octyldodecanol, isostearyl alcohol, 2-butyloctanol, 2-hexyldecanol, 2-undecylpentadecanol or oleyl alcohol;

higher fatty acids, such as oleic acid, linoleic acid or linolenic acid;

carbonates;

acetates;

citrates.

Among the volatile silicones, mention may be made of volatile linear or cyclic silicone oils, especially those with a viscosity ≤8 centistokes ($8 \times 10^{-6}$ m²/s) and especially containing from 2 to 7 silicon atoms, these silicones optionally comprising alkyl or alkoxy groups containing from 1 to 10 carbon atoms. As volatile silicone oils that may be used in the invention, mention may be made especially of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Mention may also be made of the volatile linear alkyltrisiloxane oils of general formula (I):

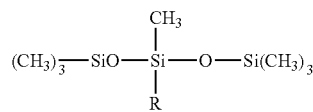

where R represents an alkyl group comprising from 2 to 4 carbon atoms, one or more hydrogen atoms of which may be replaced with a fluorine or chlorine atom.

As examples of non-volatile silicone oils, mention may be made of linear or cyclic non-volatile polydimethylsiloxanes (PDMS); polydimethylsiloxanes comprising alkyl, alkoxy or phenyl groups, which are pendent or at the end of a silicone chain, these groups containing from 2 to 24 carbon atoms; phenyl silicones, for instance phenyl trimethicones, phenyl dimethicones, phenyl trimethylsiloxy diphenyl siloxanes, diphenyl dimethicones, diphenyl methyldiphenyl trisiloxanes and 2-phenylethyl trimethylsiloxy silicates, and mixtures thereof. Use will be made more particularly of a linear non-volatile polydimethylsiloxane (PDMS).

Preferably, the oily phase comprises at least one non-volatile hydrocarbon-based oil and optionally at least one non-volatile silicone oil.

The hydrocarbon-based oil will preferably be chosen from triglycerides such as caprylic/capric acid triglycerides, fatty acid esters such as isopropyl palmitate and ethers such as dimethyl ether, and alkanes such as isohexadecane, and mixtures thereof.

The hydrocarbon-based oil(s) will preferably be present in the composition in concentrations ranging from 5% to 30% by weight and more preferentially ranging from 5% to 20% by weight relative to the total weight of the composition.

The concentration of the oily phase preferably ranges from 10% to 90% by weight and more preferentially from 10% to 30% by weight, relative to the total weight of the composition.

According to a particularly preferred form of the invention, the composition is in the form of an oil-in-water emulsion comprising, in a cosmetically acceptable medium:

A) a continuous aqueous phase and

B) an oily phase dispersed in the said aqueous phase and comprising at least one hydrocarbon-based oil;

C) at least a mixture consisting of:
  i) at least one nonionic surfactant containing a saturated linear hydrocarbon-based chain comprising at least 16 carbon atoms, the said surfactant being other than a fatty alcohol, and
  ii) at least one fatty alcohol in pure form containing at least 16 carbon atoms or a mixture consisting exclusively of fatty alcohols containing at least 16 carbon atoms;

D) at least one wax with a melting point of greater than 45° C. comprising one or more $C_{40}$-$C_{70}$ ester compounds and not comprising any $C_{20}$-$C_{39}$ ester compounds, and E) at least one water-soluble polysaccharide as defined previously and F) optionally at least one nonionic associative polymer as defined previously.

The term "fatty alcohol" means any non-alkoxylated alcohol comprising a linear saturated hydrocarbon-based chain, in particular consisting of a linear alkyl chain, the said chain comprising at least 10 carbon atoms and a hydroxyl function.

The term "hydrocarbon-based chain" means an organic group predominantly consisting of hydrogen atoms and carbon atoms.

The term "pure fatty alcohol comprising at least 16 carbon atoms" means any non-alkoxylated alcohol consisting of more than 95% by weight of the said alcohol, the said alcohol comprising a saturated linear hydrocarbon-based chain and in particular consisting of a linear alkyl chain, the said chain comprising at least 16 carbon atoms and a hydroxyl function.

The term "mixture consisting exclusively of fatty alcohols comprising at least 16 carbon atoms" means any mixture comprising at least two non-alkoxylated alcohols comprising a linear saturated hydrocarbon-based chain, in particular consisting of a linear or branched alkyl chain, the said chain comprising at least 16 carbon atoms and a hydroxyl function; the said fatty alcohol mixture containing less than 1% by weight and preferably less than 0.5% by weight of $C_{12}$-$C_{15}$ fatty alcohol relative to the total weight of the fatty alcohol mixture, or even being free of $C_{12}$-$C_{15}$ fatty alcohol.

The term "ester compound" means any organic molecule comprising a linear or branched, saturated or unsaturated hydrocarbon-based chain comprising at least one ester function of formula —COOR in which R represents a hydrocarbon-based radical, in particular a saturated linear alkyl radical.

The term "wax not comprising any $C_{20}$-$C_{39}$ ester compounds" means any wax containing less than 1% by weight and preferably less than 0.5% by weight of $C_{20}$-$C_{39}$ ester compounds relative to the weight of the wax, or even being free of $C_{20}$-$C_{39}$ ester compounds.

Melting Point

For the purposes of the invention, the melting point corresponds to the temperature of the most endothermic peak observed in thermal analysis (DSC) as described in the standard ISO 11357-3; 1999. The melting point of the surfactant or of the wax can be measured using a differential scanning calorimeter (DSC), for example the calorimeter sold under the name MDSC 2920 by TA Instruments.

The Measurement Protocol is as Follows:

A sample of 5 mg of wax placed in a crucible is subjected to a first temperature rise ranging from −20° C. to 100° C., at a heating rate of 10° C./minute, is then cooled from 100° C. to −20° C. at a cooling rate of 10° C./minute and is finally subjected to a second temperature rise ranging from −20° C. to 100° C. at a heating rate of 5° C./minute. During the second temperature increase, the variation in the difference in power absorbed by the empty crucible and by the crucible containing the sample of wax is measured as a function of the temperature. The melting point of the compound is the temperature value corresponding to the top of the peak of the curve representing the variation in the difference in power absorbed as a function of the temperature.

Mixture of Surfactants and of Fatty Alcohol

Nonionic Surfactants

The nonionic surfactants in accordance with the invention contain a saturated linear chain comprising at least 16 carbon atoms.

Among these nonionic surfactants, examples that may be mentioned include:
  alkylpolyglucosides in which the alkyl chain comprises at least 20 carbon atoms;
  ethoxylated fatty alcohols comprising at least 20 carbon atoms;
  polyglyceryl fatty esters containing a chain comprising at least 20 carbon atoms;
  mixtures thereof.

The alkylpolyglucosides generally correspond to the following structure:

$$R(O)(G)_x$$

in which the radical R is a linear or branched alkyl radical containing at least 20 carbon atoms, G is a saccharide residue and x ranges from 1 to 5, preferably from 1.05 to 2.5 and more preferentially from 1.1 to 2.

The saccharide residue may be chosen from glucose, dextrose, saccharose, fructose, galactose, maltose, maltotriose, lactose, cellobiose, mannose, ribose, dextran, talose, allose, xylose, levoglucan, cellulose and starch. More preferentially, the saccharide residue denotes glucose.

It should also be noted that each unit of the polysaccharide part of the alkylpolyglycoside may be in α or β isomer form, in L or D form, and the configuration of the saccharide residue may be of furanoside or pyranoside type.

It is, of course, possible to use mixtures of alkylpolysaccharides, which may differ from each other in the nature of the borne alkyl unit and/or the nature of the bearing polysaccharide chain.

Among the alkylpolyglycosides that may be used according to the invention, mention may be made of cetearylglucoside, such as that present in the commercial product Montanov 68® from SEPPIC or Tegocare CG90 from Evonik, and arachidylpolyglucoside such as that present in the commercial product Montanov 202® from the company SEPPIC.

Among the ethoxylated fatty alcohols that may be used according to the invention, mention may be made of Beheneth-10, such as the commercial product Eumulgin BA 10 from Cognis.

Among the polyglyceryl fatty esters, mention may be made of polyglyceryl-6 behenate, such as the commercial product Pelemol 6G22 from Phoenix Chemical or polyglyceryl-10 behenate/eicosadiate, such as the commercial product Nomcort HK-P from Nisshin Oillio.

Use will be made more particularly of alkylpolyglucosides and preferably $C_{16}$-$C_{18}$ alkylpolyglucosides such as cetearylglucoside, and $C_{20}$-$C_{22}$ alkylpolyglucosides such as arachidylpolyglucoside, and more particularly arachidylpolyglucoside.

Fatty Alcohols

The fatty alcohols in accordance with the invention are chosen from:
  a pure fatty alcohol comprising at least 16 carbon atoms;
  a mixture consisting exclusively of fatty alcohols containing at least 16 carbon atoms.

Mixtures consisting exclusively of fatty alcohol(s) containing at least 16 atoms will be chosen more particularly.

The pure fatty alcohols in accordance with the invention containing at least 16 carbon atoms preferably comprise from 16 to 26 carbon atoms and more preferentially from 16 to 22 carbon atoms.

Among the pure fatty alcohols in accordance with the invention containing more than 16 carbon atoms, mention may be made of:
  cetyl alcohol, for instance the commercial products Cetanol from the company Kokyu Alcohol Kogyo Co., Ltd and Alfol 16 Alcohol® from the company Sasol Germany GmbH (Hamburg)
  stearyl alcohol, for instance the commercial product Kalcol 80-98® from Kao,
  arachidyl alcohol, for instance the commercial products Hainol 20SS® from the company Kokyu Alcohol Kogyo Co. Ltd and Nacol 20-95® from the company Sasol Germany GmbH (Hamburg),
  behenyl alcohol, for instance the commercial products Nacol 22-97® and Nacol 22-98® from the company Sasol Germany GmbH (Hamburg)
  and mixtures thereof.

Among the mixtures of fatty alcohols in accordance with the invention containing at least 16 carbon atoms, mention may be made of:
  cetearyl alcohols (mixture of cetyl alcohol and stearyl alcohol) such as the mixture comprising 70% by weight of $C_{18}$ fatty alcohol(s) and 30% by weight of $C_{16}$ fatty alcohol(s), such as the commercial product Nafol 1618 S® (Sasol Germany GmbH Hamburg)

mixtures based on at least one $C_{22}$ fatty alcohol, at least one $C_{20}$ fatty alcohol and at least one $C_{18}$ fatty alcohol, a mixture of arachidyl alcohol and behenyl alcohol.

Among the mixtures based on at least one $C_{22}$ fatty alcohol, at least one $C_{20}$ fatty alcohol and at least one $C_{18}$ fatty alcohol, mention may be made of:

the mixture comprising 77% by weight of $C_{22}$ fatty alcohol(s), 18% by weight of $C_{20}$ fatty alcohol(s) and 5% by weight of $C_{18}$ fatty alcohol(s), such as the product Nafol 1822 C Alcohol® (Sasol Germany GmbH Hamburg) or the commercial product Lanette 22® (Cognis Corporation Care Chemicals);

the mixture comprising 80% by weight of $C_{22}$ fatty alcohol(s), 10% by weight of $C_{20}$ fatty alcohol(s) and 10% by weight of $C_{18}$ fatty alcohol(s), such as the commercial product Behenyl Alcohol 80® (Kokyu Alcohol Kogyo Co. Ltd);

the mixture comprising 44% by weight of $C_{22}$ fatty alcohol(s), 11% by weight of $C_{20}$ fatty alcohol(s) and 43% by weight of $C_{18}$ fatty alcohol(s), such as the commercial product Nafol 1822 Alcohol® (Sasol Germany GmbH Hamburg);

the mixture comprising 6% by weight of $C_{24}$ fatty alcohol(s), 30% by weight of $C_{22}$ fatty alcohol(s), 58% by weight of $C_{20}$ fatty alcohol(s) and 7% by weight of $C_{18}$ fatty alcohol(s), such as the commercial product Nafol 20-22 EN (Sasol Germany GmbH Hamburg).

Use will be made more particularly of behenyl alcohol, arachidyl alcohol or a cetostearyl alcohol, or mixtures thereof.

As mixture of nonionic surfactant and of fatty alcohol in accordance with the invention, mention may be made of:

a mixture of arachidyl alcohol, behenyl alcohol and arachidylglucoside, such as the commercial product Montanov 202® from the company SEPPIC, a mixture of cetearyl alcohol and cetearylglucoside, for instance the commercial product Montanov 68® from the company SEPPIC or the combination of Tegocare CG90 with Nafol 1822 C.

Use will be made more particularly of a mixture of arachidyl alcohol, behenyl alcohol and arachidylglucoside, such as the commercial product Montanov 202® from the company SEPPIC.

The fatty alcohol/nonionic surfactant mixture is preferably present in the emulsions in accordance with the invention in active material concentrations ranging from 1% to 10% by weight and more preferentially from 2% to 7% by weight relative to the total weight of the emulsion.

The fatty alcohol/nonionic surfactant mixture preferably contains more than 50% by weight of fatty alcohol(s) and more preferentially more than 70% by weight of fatty alcohol(s) relative to the total weight of the said fatty alcohol/nonionic surfactant mixture.

Additives

The compositions according to the invention may also furthermore comprise additional cosmetic and dermatological active agents.

The cosmetic compositions according to the invention may comprise cosmetic adjuvants chosen from opacifiers, stabilizers, preserving agents, polymers, fragrances, sunscreens, dermatological or cosmetic active agents, fillers, suspension agents, dyestuffs or any other ingredient usually used in cosmetics for this type of application.

Among the fillers, mention may be made of talc, kaolin, silicas, clays, perlite and water-insoluble particulate starches.

Among the silicas, mention may be made of:

porous silica microspheres. The spherical porous silica microparticles preferably have a mean particle size ranging from 0.5 to 20 µm and more particularly from 3 to 15 µm. They preferably have a specific surface area ranging from 50 to 1000 $m^2/g$ and more particularly from 150 to 800 $m^2/g$. They preferably have a specific pore volume ranging from 0.5 to 5 ml/g and more particularly from 1 to 2 ml/g. Examples of porous silica microbeads that may be used include the following commercial products:

Silica Beads SB 150® from Miyoshi

Sunsphere H-51®; Sunsphere H53® and Sunsphere H33® from Asahi Glass MSS-500-3H® from the company Kobo Sunsil 130® from Sunjin Spherica P-1500® from Ikeda Corporation Sylosphere® from Fuji Silysia polydimethylsiloxane-coated amorphous silica microspheres, especially those sold under the name SA Sunsphere® H33 amorphous hollow silica particles, especially those sold under the name Silica Shells by the company Kobo precipitated silica powders surface-treated with a mineral wax, such as precipitated silica treated with a polyethylene wax, and especially those sold under the name Acematt OR 412 by the company Evonik-Degussa.

Of course, a person skilled in the art will take care to choose this or these optional additional compounds so that the advantageous properties intrinsically attached to the cosmetic composition in accordance with the invention are not, or not substantially, detrimentally affected by the envisaged addition or additions.

The dermatological or cosmetic active agents may be chosen especially from moisturizers, desquamating agents, agents for improving the barrier function, depigmenting agents, antioxidants, dermo-decontracting agents, anti-glycation agents, agents for stimulating the synthesis of dermal and/or epidermal macromolecules and/or for preventing their degradation, agents for stimulating fibroblast or keratinocyte proliferation and/or keratinocyte differentiation, agents for promoting the maturation of the horny envelope, NO-synthase inhibitors, peripheral benzodiazepine receptor (PBR) antagonists, agents for increasing the activity of the sebaceous glands, agents for stimulating the energy metabolism of cells, tensioning agents, lipo-restructuring agents, slimming agents, agents for promoting the cutaneous capillary circulation, calmatives and/or anti-irritants, sebo-regulators or anti-seborrhoeic agents, astringents, cicatrizing agents, anti-inflammatory agents, keratolytic agents, agents for preventing hair regrowth and antiacne agents.

Galenical Forms

The compositions according to the invention may be in the form of a gel or cream whose consistency may vary as a function of the desired application, such as a cosmetic product for caring for, holding or colouring the skin or the hair, or a body hygiene product, especially such as a deodorant and/or antiperspirant.

To extract the product from the container, a pressure is exerted on the container in order to push the product out of the container via the dispensing orifice. The product is then collected before being applied to the keratin surface.

Deodorant and/or Antiperspirant Compositions

The present invention also relates to a cosmetic process for treating human perspiration and/or perspiration-related body odour, which consists in applying to the surface of a human keratin material a composition comprising at least one deodorant active agent and/or antiperspirant active agent dispensed by the device as defined previously.

Additional Antiperspirant Salts or Complexes

The aluminium and/or zirconium antiperspirant salts or complexes are preferably chosen from aluminium halohydrates, aluminium and zirconium halohydrates, complexes of zirconium hydroxychloride and of aluminium hydroxychloride with or without an amino acid, such as those described in U.S. Pat. No. 3,792,068.

Among the aluminium salts, mention may be made in particular of aluminium chlorohydrate in activated or unactivated form, aluminium chlorohydrex, the aluminium chlorohydrex-polyethylene glycol complex, the aluminium chlorohydrex-propylene glycol complex, aluminium dichlorohydrate, the aluminium dichlorohydrex-polyethylene glycol complex, the aluminium dichlorohydrex-propylene glycol complex, aluminium sesquichlorohydrate, the aluminium sesquichlorohydrex-polyethylene glycol complex, the aluminium sesquichlorohydrex-propylene glycol complex, aluminium sulfate buffered with sodium lactate and aluminium lactate.

Among the aluminium-zirconium salts, mention may be made in particular of aluminium zirconium octachlorohydrate, aluminium zirconium pentachlorohydrate, aluminium zirconium tetrachlorohydrate and aluminium zirconium trichlorohydrate.

The complexes of zirconium hydroxychloride and of aluminium hydroxychloride with an amino acid are generally known as ZAG (when the amino acid is glycine). Among these products, mention may be made of the aluminium zirconium octachlorohydrex-glycine complexes, the aluminium zirconium pentachlorohydrex-glycine complexes, the aluminium zirconium tetrachlorohydrex-glycine complexes and the aluminium zirconium trichlorohydrex-glycine complexes.

The aluminium and/or zirconium antiperspirant salts or complexes may be present in the composition according to the invention in a proportion of at least 0.5% by weight and preferably from 0.5% to 25% by weight relative to the total weight of the composition.

Deodorant Active Agents

The compositions according to the invention may also furthermore contain one or more additional deodorant active agents.

The term "deodorant active agent" refers to any substance that is capable of masking, absorbing, improving and/or reducing the unpleasant odour resulting from the decomposition of human sweat by bacteria.

The deodorant active agents may be bacteriostatic agents or bactericides that act on underarm odour microorganisms, such as 2,4,4'-trichloro-2'-hydroxydiphenyl ether (®Triclosan), 2,4-dichloro-2'-hydroxydiphenyl ether, 3',4',5'-trichlorosalicylanilide, 1-(3',4'-dichlorophenyl)-3-(4'-chlorophenyl)urea (®Triclocarban) or 3,7,11-trimethyldodeca-2,5,10-trienol (®Farnesol); quaternary ammonium salts such as cetyltrimethylammonium salts, cetylpyridinium salts, DPTA (1,3-diaminopropanetetraacetic acid), 1,2-decanediol (Symclariol from the company Symrise), glycerol derivatives, for instance caprylic/capric glycerides (Capmul MOM from Abitec), glyceryl caprylate or caprate (Dermosoft GMCY and Dermosoft GMC, respectively from Straetmans), polyglyceryl-2 caprate (Dermosoft DGMC from Straetmans), and biguanide derivatives, for instance polyhexamethylene biguanide salts. chlorhexidine and salts thereof; 4-phenyl-4,4-dimethyl-2-butanol (Symdeo MPP from Symrise); cyclodextrins.

Among the deodorant active agents in accordance with the invention, mention may also be made of—zinc salts, for instance zinc salicylate, zinc gluconate, zinc pidolate; zinc sulfate, zinc chloride, zinc lactate, zinc phenolsulfonate; zinc ricinoleate;

sodium bicarbonate;

salicylic acid and derivatives thereof such as 5-n-octanoylsalicylic acid;

zeolites, especially silver-free metallic zeolites;

alum;

triethyl citrate.

The deodorant active agents may preferably be present in the compositions according to the invention in weight concentrations ranging from 0.01% to 10% by weight relative to the total weight of the composition.

Dispensing Device

A dispensing device that is particularly suited to this composition will be described with reference to the attached drawings, in which.

Throughout the following text, the terms "upstream" and "downstream" are understood generally to mean with respect to the normal direction of circulation of a fluid, in particular a cosmetic product.

The device 310 is intended to store, dispense and apply the cosmetic composition onto a keratin surface, especially the skin, of a user.

Figure 2:
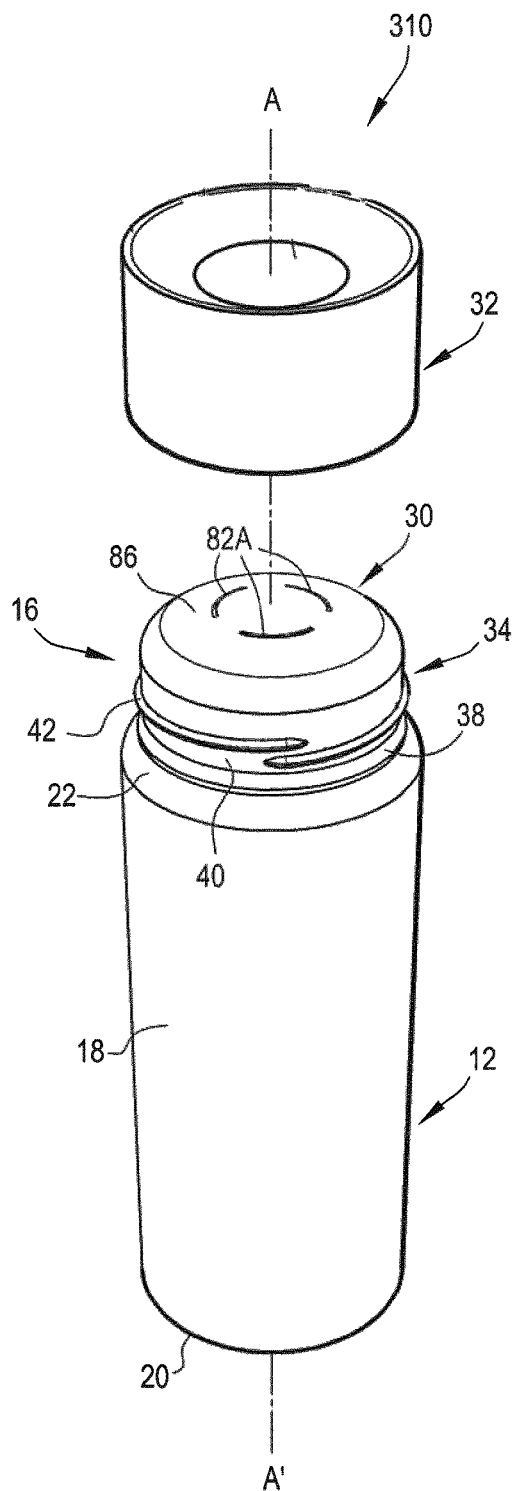
FIG. 2 is a perspective view of three-quarters of the face of the device of FIG. 1, the lid having been removed from the dispensing head.

The dispensing device 310 comprises a container 12 delimiting an inner volume 14 for receiving the cosmetic product, and a head 16 for dispensing cosmetic product, closing off the container 12 (visible in FIG. 2).

Figure 1:
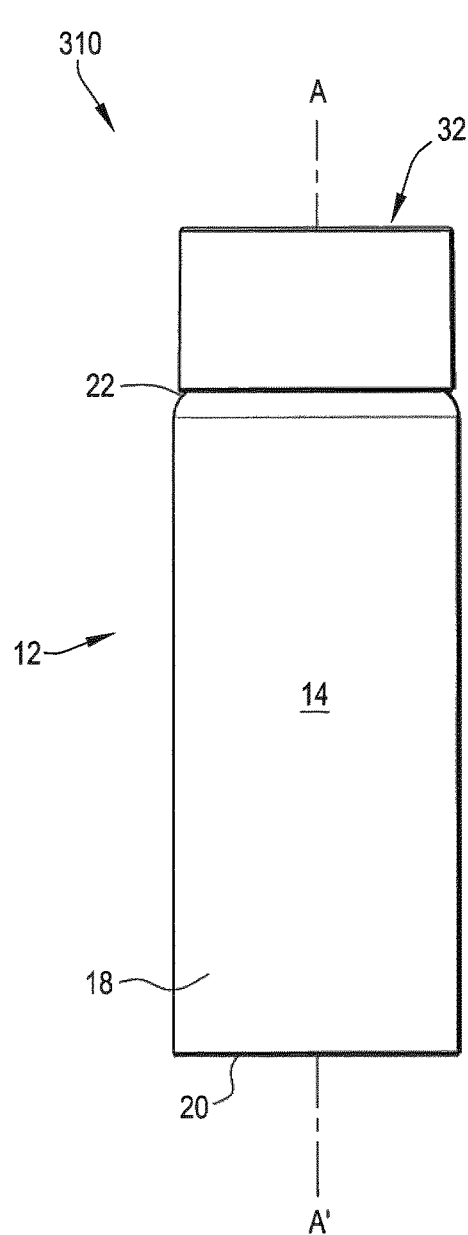
FIG. 1 is a side view of a dispensing device, the lid occupying its closing-off position.

In the example shown in FIGS. 1 and 2, the container 12 comprises a wall 18 which advantageously forms a tube. The wall 18 is closed off in leaktight manner at its upstream end 20 opposite the head 16. At its downstream end 22, the wall 18 is closed off by the head 16.

The base of the wall 18 is advantageously closed by pinching and by soldering the wall 18.

The wall 18 is deformable. The term "deformable" means that the wall can be deformed when pressed by the user, for example when it is squeezed between a user's fingers.

The wall may be sufficiently rigid to return to its initial position when the exerted pressure is released, for example when the wall is made of a mixture of polyethylene (PE) comprising 30% low-density polyethylene (LDPE) and 70% high-density polyethylene (HDPE). The advantage of having a sufficiently rigid wall is that it affords the user a good grip on the device to facilitate the application of the product.

As a variant, it is possible for the wall not to return to its initial position when the pressure is released; in this case, the wall remains in its deformed position, for example when the wall is made mainly of low-density polyethylene (LDPE) or of a metallic material.

The container 12 extends along a longitudinal general axis A-A' between the ends 20, 22.

Advantageously, the head 14 is engaged on the neck of the container 12 and is attached to the neck by click-fastening. To this end, the head 14 is click-fastened onto the neck of the container 12 and is held on the neck by stops.

As a variant, the head 16 is attached by soldering, or by overmoulding of the wall 18 of the container 12 onto the head 14. In another variant, the head 14 and the container 12 are at least partially made from the same material.

The inner volume 14 is delimited inside the container 12. It contains the cosmetic composition.

When the user wishes to apply cosmetic product, he extracts the cosmetic product present in the inner volume 14 by generating a pressure of product in the inner volume 14, for example by exerting a pressure on the deformable wall of the container 12.

As a variant, not shown, the container is a tube comprising an inner deformable pocket making it possible to delimit a volume containing the cosmetic composition and a volume not containing any composition in the container. The deformable wall of the tube is closed off at its upstream end onto the dispensing head and is closed at its downstream end. The wall of the tube may have an air intake orifice in communication with the inner volume of the container not containing any composition. The deformable wall of the tube is sufficiently rigid to return to its initial position when the exerted pressure is released, whereas it is possible for the pocket, for its part, not to return to its initial position. The volume containing the composition is in communication with the dispensing head. Thus, to dispense the composition, the user exerts a pressure on the tube while holding, for example, a finger over the air intake orifice to close it off. The excess air pressure generated in the tube, especially in the volume not containing any composition, is then exerted on the pocket and on the volume of the container containing the composition so as to expel the product via the dispensing head.

Figure 3:
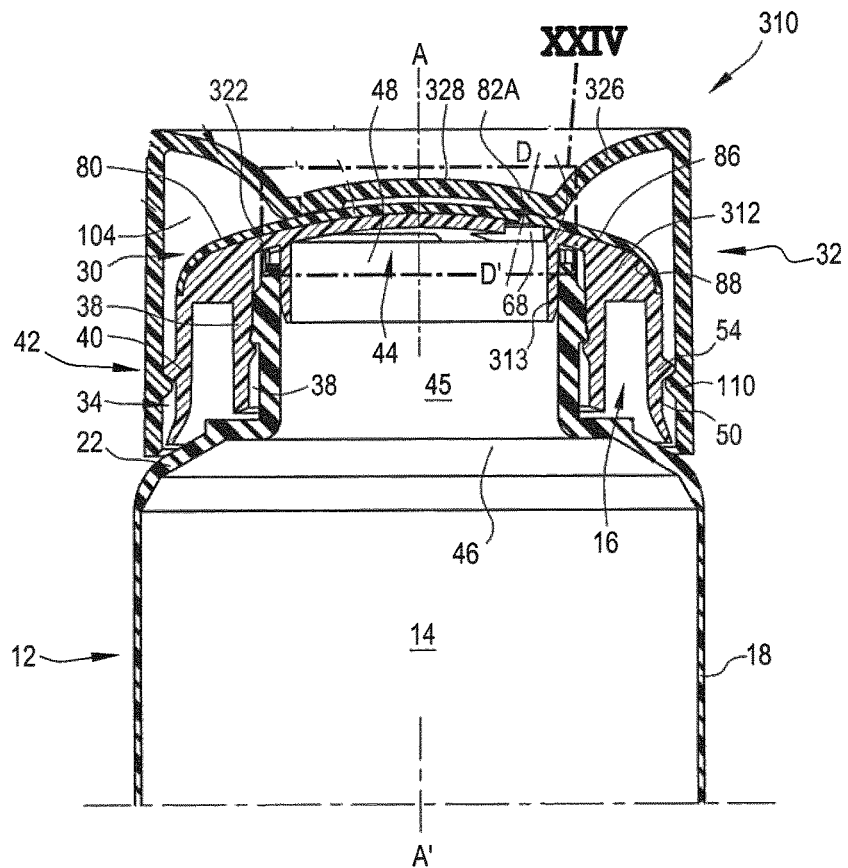
FIG. 3 is a view in cross section along a vertical median plane of the device of FIG. 1.
Figure 11:
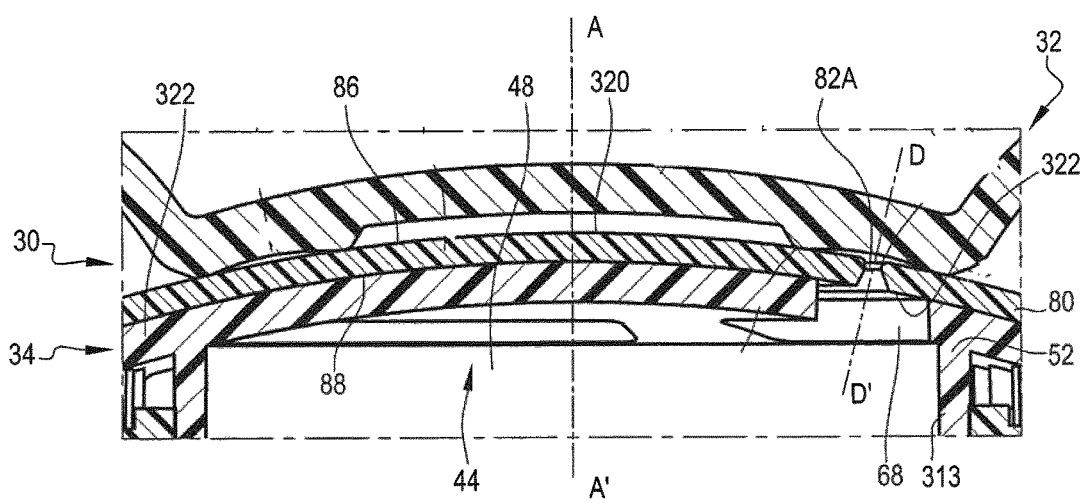
FIG. 11 is a view of a detail labelled XXIV in FIG. 3.

As illustrated in FIGS. 2, 3 and 11, the head 14 comprises an application wall 30 and optionally a lid 32 intended to cover the application wall 30. It advantageously comprises a support 34 bearing the application wall 30.

As illustrated in FIG. 3, the support 34 comprises an inner skirt 38 connected to the wall 18 of the container 12, and an outer sleeve 40 for attaching the lid 32 fitted around the skirt 38. The support 34 also comprises at least one member 42 for retaining the lid 32 on the support 34 and, with reference to FIG. 6, a perforated reinforcement 44 for holding the application wall 30.

In this example, the support 34 is made as a single piece, being made from the same material. It is made, for example, by injection moulding using a thermoplastic material that is more rigid than that forming the application wall 30, such as polyethylene (PE), polypropylene (PP), or mixtures thereof. As a variant, the support 34 directly forms the application wall 30.

The skirt 38 delimits a central product circulation passage 45 which emerges via an upstream aperture 46 via a downstream aperture 48. The circulation passage 45 extends downstream the inner volume 14.

The sleeve 40 comprises a peripheral tubular wall 50 and a downstream bridge 312 connecting it to the skirt 38. The skirt 38 advantageously delimits an annular rim 52 which partially projects towards the axis A-A', the rim 52 being extended upstream by a sealing skirt 313 inserted in the neck of the container 12 to retain the product.

In this example, the support 34 has a cross section of circular outer contour. As a variant, the outer contour is elongated, for example oval or polygonal.

In the example shown in the figures, the lid 32 can be screwed onto the support 34. The retaining member 42 is then formed by a thread 54 projecting radially outwards relative to the sleeve 40. As a variant, the lid 32 is click-fastened onto the support 34. When it is present, the retaining member 42 is formed, for example, by click-fastening or holding means by gripping the lid 32.

The reinforcement 44 projects transversely into the passage 45 at the downstream aperture 48. It is rigid or semi-rigid.

The reinforcement 44 is perforated. In the example illustrated in FIG. 6, the reinforcement 44 comprises an inner disk 62 and a plurality of outer lugs 64 for connecting between the rim 52 of the skirt 38 and the reinforcement 44.

The outer lugs 64 connect the rim 52 of the skirt 38 to the disk 62. They define, between the skirt 38 and the disk 62, a plurality of outer apertures 68 for the passage of product.

In this example, the outer lugs 64 define several C-shaped apertures 68 opening towards each other facing the axis A-A'.

In this example, the number of apertures 68 is equal to 3. More generally, this number is between 1 and 10.

The inner disk 62 has an outer contour contained in the inner contour of the skirt 38.

The application wall 30 is advantageously formed by a body 80 made of polymeric material. The thickness of the body 80 is, for example, less than 5 mm. The body 80 is advantageously made from an elastomer, such as elastomer, thermoplastic or thermoplastic elastomer material, PEBD, PVC, PU, thermoplastic elastomer polyesters, especially copolymers of butene terephthalate and of esterified polytetramethylene glycol oxide, Hytrel®, EPDM, PDM, EVA, SIS, SEBS, SBS, latex, silicone, nitrile, butyl, polyurethane, polyether block amide, polyester or a copolymer of ethylene and of α-olefin.

The support 34 and the wall 30 are advantageously formed by twin injection of material. In one variant, the support 34 and the wall 30 are formed by injection of the same material.

In this example, the body 80 has an outer contour whose shape is substantially complementary to the outer contour of the support 34. It is thus capable of covering the support 34 to close off the downstream aperture 48.

In this example, the body 80 has a convex dome shape, of convexity directed downstream. It bears at its periphery on the support and is attached thereto. To this end, it is applied to the annular rim 52 and to the bridge 312.

In addition, the body 80 rests on the perforated reinforcement 44, being attached thereto.

The convex dome advantageously has a circular contour, for example with a diameter of greater than 20 mm, better still greater than 30 mm, for example equal to 35 mm. The radius of curvature of the convex dome is, for example, between 30 mm and 150 mm.

Figure 4:
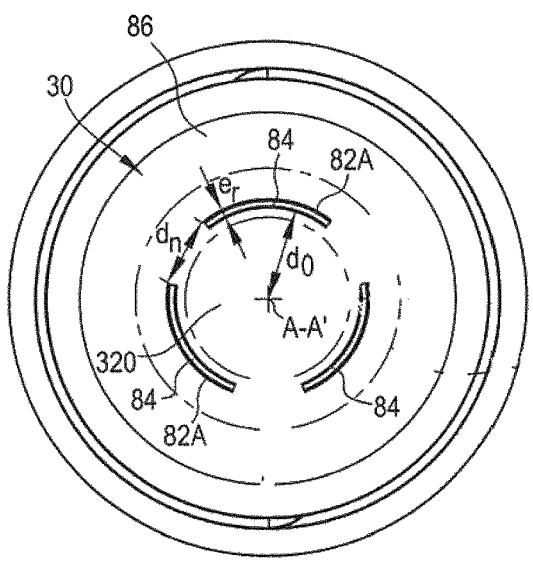
FIG. 4 is a top view of the dispensing head of the device of FIG. 1.
Figure 5:
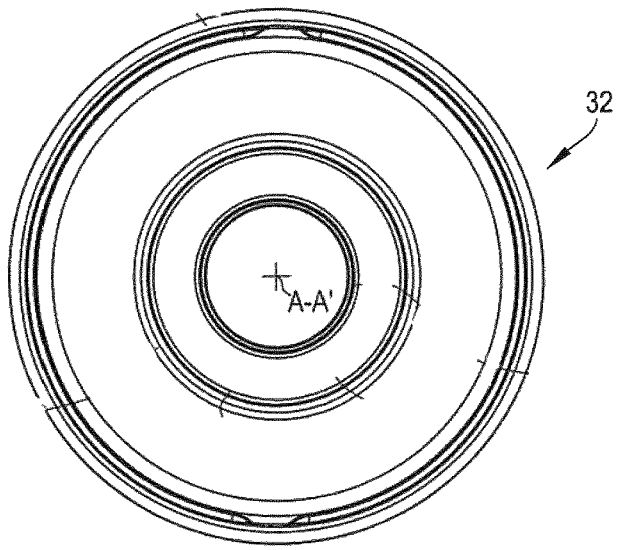
FIG. 5 is a bottom view of the lid for closing off the device of FIG. 1.
Figure 6:
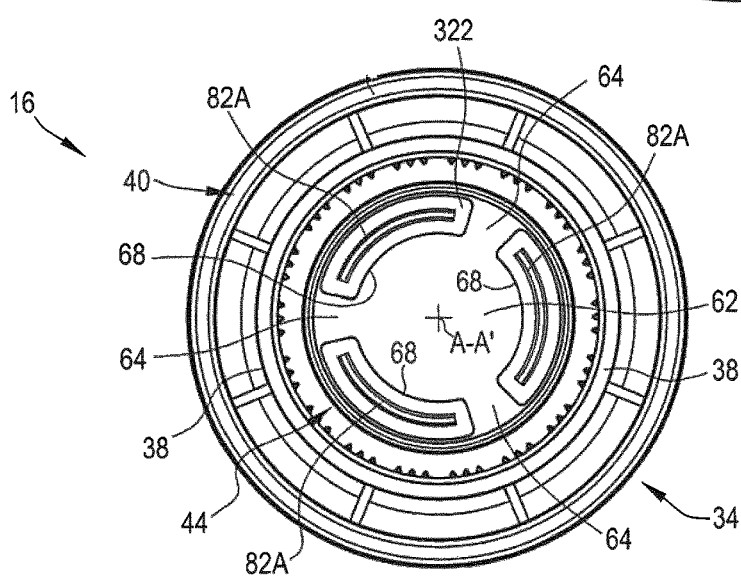
FIG. 6 is a bottom view of the head of the device of FIG. 1.

As illustrated by FIGS. 4 and 6, the body 80 of the wall 30 delimits at least one product dispensing orifice 82A, passing through the body 80 to emerge facing the downstream aperture 48, advantageously facing the passage apertures 68 made in the reinforcement 44.

In the example represented in the figures, the body 80 of the application wall 30 delimits a plurality of dispensing orifices 82A, which are especially C-shaped.

The orifices 82A advantageously extend facing the apertures 68.

In this example, the dispensing orifices 82A are formed by incurved slits 84 made through the body 80 between a downstream surface 86 of the body 80 and an upstream surface 88 of the body 80. The downstream surface 86 forms the application surface of the convex dome.

In this example, the slits 84 extend, in section in a median plane, along a general axis D-D' corresponding to a normal N to the downstream surface 86, taken at the outlet of the slit 84. As a variant, the slits 84 extend along an axis D-D' which is inclined relative to a normal N to the downstream surface 86.

As illustrated in FIG. 4, the dispensing orifices 82A are eccentric relative to the central axis A-A' of the wall 30. The central axis A-A' is defined as the axis passing through the centre of the downstream surface 86 of the wall 30, normal to this surface. In this example, the central axis A-A' is the same as the general axis A-A' of the container 12.

The distance do radially separating the axis A-A' of each orifice 82A is greater than the maximum radial extent er of each orifice 82A. Thus, as illustrated by FIG. 17, the wall 30 has a solid central zone 320, lacking an orifice 82A, in particular at the axis A-A'.

The slits 84 have a length which is very much greater than their radial extent er. Thus, the length of each slit 84 is at least greater than twice the maximum radial extent er of the slit 84. It should be noted that the radial extent er is then the smallest transverse dimension measured between two opposite edges of the dispensing orifice.

More generally, the maximum radial extent er of each orifice 82A, taken relative to the axis A-A', is less than 1.3 mm and especially less than 1 mm. This transverse extent is advantageously between 0.4 mm and 0.8 mm and better still between 0.5 mm and 0.7 mm, for example equal to 0.6 mm; in this case, the edges of each orifice 82A are permanently located separated from each other.

The length of the slits 84 may be greater than 2.5 mm, for example equal to 10 mm.

Furthermore, for each slit with a radial extent er of less than 1.3 mm, the coefficient determined by the ratio of the area of the orifice to the parameter of the said orifice may advantageously be less than 0.6, or even less than 0.4 and better still less than 0.3. The smaller this coefficient, the greater the length of the slit and the smaller its area. A large perimeter thus makes it possible to dispense product over a large extent of the application surface, whereas a small area makes it possible to limit and to control the amount of product dispensed.

The orifices 82A are disjointed, i.e. they are separated from each other by solid regions of the application wall 30. In this example, the minimum distance do separating two adjacent orifices 82A is greater than the maximum radial extent er of each orifice 82A.

In the example of FIG. 4, the orifices 82A are angularly distributed around the axis A-A' along a circumference around this axis.

The angular extent of each orifice 82A taken around the axis A-A' is less than 360°/N in which N is the number of orifices 82A on a circumference. The angular extent of each orifice 82A is especially less than (360°−10N)/N.

Each dispensing orifice 82A is placed facing an aperture 68.

However, each orifice 82A has an area less than the area of the aperture 68 opposite which it is placed. Thus, as illustrated in FIG. 6, the wall 30 defines about each orifice 82A, and facing the aperture 68, a peripheral rim 322.

As a variant, each orifice 82A has an extent substantially equal to the aperture 68 opposite which it is placed. In yet another variant, the orifice 82A is located along an edge of the aperture 68, being off-centred relative to the aperture 68. In this case, the peripheral rim 322 has a substantial width and is capable of directing the dispensing of product through the orifice 82A to improve its distribution over the downstream surface 86.

In the example represented in FIGS. 1 to 6, the downstream surface 86 of the wall is smooth. To this end, it is free of macroscopic roughness or unevenness.

The term "macroscopic roughness or unevenness" means roughness or unevenness with a thickness, taken perpendicular to a normal to the wall 30, greater than the thickness of the wall 30.

Thus, the wall 30 is capable of gliding over a user's skin. It is especially free of macroscopic roughness or unevenness at the periphery of the apertures 82A, which allows pleasant application of product over an area of the user's body.

In the dispensing position, a lid 32 is provided separated from the support 34 and from the application wall 30.

In this position, and as will be seen hereinbelow, the dispensing orifices 82A are freed to allow the passage of cosmetic product from the inner volume 14 through the passage 45 to the downstream surface 86 of the application wall.

In the example in which the lid 32 is intended to be screwed onto the support 34, the additional retaining member 110 is formed by a thread additional to the thread present on the support 34.

The application wall 30 is advantageously manufactured as a single piece by moulding.

The orifices 82A, 82B are then manufactured, either during the moulding of the application wall 30, or subsequent to this moulding, by making apertures via laser or mechanical cutting of the wall 30.

The use of a flexible material to make the application wall 30 ensures that the moulding of the orifices 82A, 82B can be performed simply.

The device 310 according to the invention functions as follows.

Initially, when the device 310 is stored, the lid 32 occupies its closing-off position engaged on the support 34, as shown in FIG. 1. The application wall 30 is received in an upstream volume 104. The retaining members 54, 110 co-operate together to hold the lid 32 in position relative to the support 34 and relative to the application wall 30.

When the user wishes to apply cosmetic product, he removes the lid 32 to separate it from the head 16. Next, he extracts the cosmetic product present in the inner volume 14 by generating a pressure of product in the inner volume 14.

The cosmetic product present in the container 12 then passes into the passage 45. It then flows through the orifices 82A to the downstream surface 86 of the application wall 30. The cosmetic product can raise the rim 322 around the orifice 82A.

The cosmetic product then becomes deposited on the downstream surface 86.

The user brings the downstream surface 86 of the application wall 30 in contact with a body surface, for example in contact with the skin. The cosmetic product is then applied to the body surface.

When the user has finished applying product, he returns the lid 32 to its closing-off position.

In one variant, the downstream surface 86 of the application wall is textured. It has, for example, a plurality of hollows and bumps, like on a golf ball.

Figure 7:
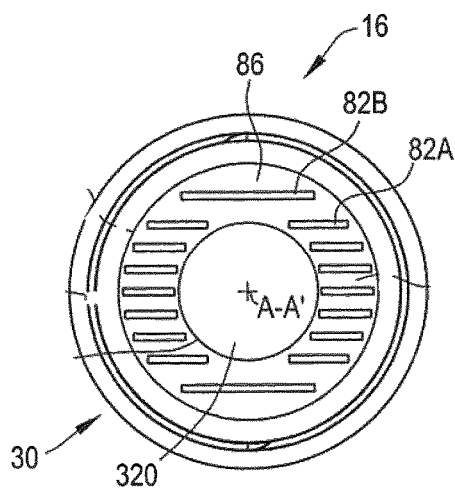
FIGS. 7 to 10 are views similar to FIG. 4 of dispensing head variants.

In one variant, illustrated, for example, by FIG. 7, the dispensing orifices 82A, 82B are rectilinear, and not incurved.

The orifices 82A, 82B have lengths that may be different from each other. For example, a first group of orifices 82A has a length shorter than that of a second group of orifices 82B.

Figure 8:
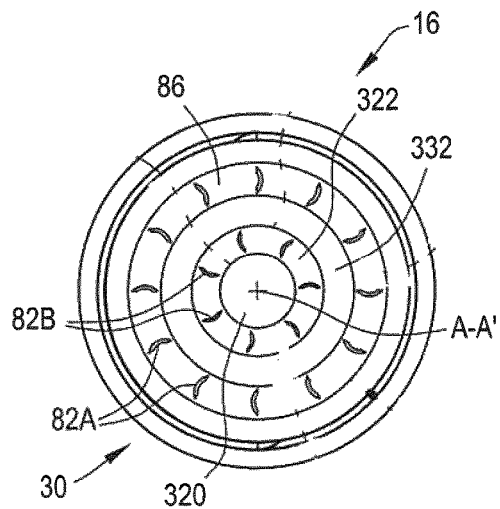

In another variant illustrated by FIG. 8, the application wall 30 delimits a first group of orifices 82A located radially outside a second group of orifices 82B.

The orifices 82A are distributed, for example, on an outer circumference of the application wall 30, whereas the orifices 82B of the second group are distributed on an inner circumference of the application wall 30.

Figure 9:
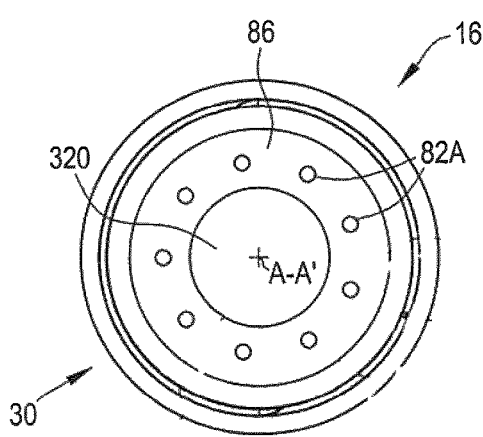

Another variant of the application head 16 is illustrated by FIG. 9. In this variant, the dispensing orifices 82A are formed by holes of circular or oblong cross section, and not by slits.

The maximum transverse dimension of each orifice 82A may be less than twice the minimum transverse dimension of the orifice 82A. Furthermore, at any point of each orifice, the smallest transverse dimension measured between two opposite edges of the orifice at this point is less than 3 mm, better still less than 1.3 mm and especially less than 1 mm. This smallest transverse dimension is advantageously between 0.4 mm and 0.8 mm and better still between 0.5 mm and 0.7 mm, for example equal to 0.6 mm. In other words, no orifice of the dispensing head comprises a point for which the smallest transverse dimension measured between two opposite edges of the orifice at this point is greater than 1.3 mm.

Figure 10:
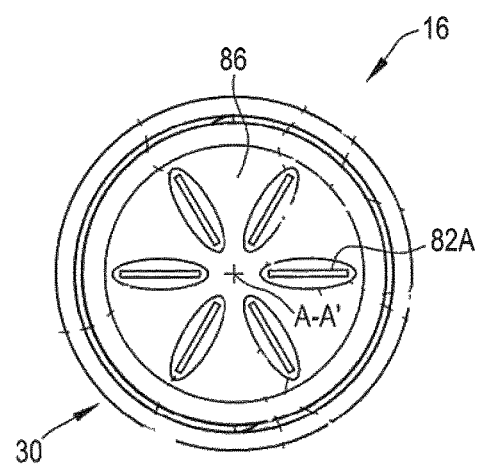

Yet another variant of the head 16 is illustrated by FIG. 10. In this variant, the dispensing orifices 82A are formed by slits extending radially relative to the centre of the applicator.

Generally, in all the embodiments, the total extent of the orifices 82A is less than 5% or even less than 2.5% of the total extent of the downstream surface 86 of the application wall 30.

The container with a deformable wall of the invention combined with a formulation of rheology described previously makes it possible to dispense a precise dose of the composition onto the application wall. Furthermore, it makes it possible to dispense the product with just one hand while at the same time applying the product to the skin.

The dimension of the dispensing orifices of the invention combined with a formulation of rheology described previously makes it possible to dispense a dose of the composition onto the application wall, by adjusting the desired amount in a precise manner by controlling the pressure generated on the container. Furthermore, with this combination, it is easier to dispense a specific dose of product by applying a substantially constant pressure in the container.

Furthermore, the dimension of the dispensing orifices combined with a formulation of rheology described previously limits the phenomenon of suction of the dose of product dispensed onto the application wall into the tube when the pressure in the container is released.

Finally, the application wall is particularly suited to distributing and spreading the composition of the invention onto the skin while at the same time conserving an immediate dry, soft, non-wetting and non-tacky feel.

The examples that follow serve to illustrate the present invention. The amounts are given as mass percentages relative to the total weight of the composition.

EXAMPLES

The examples were prepared according to the following protocol:

the aqueous phase containing the gelling agents or thickeners and the aluminium salts is heated to 80° C.;
the waxes and the surfactant mixture are heated with the oils to 80° C.;
the two phases are mixed together and sheared in a Rayneri blender for 10 minutes;
the filler is then added while blending with a Rayneri deflocculator;
the formulation is cooled to room temperature while blending with a Rayneri deflocculator, before being conditioned in a device in the form of a flexible tube according to the invention.

| Phase | Ingredients | Example 1 (invention) | Example 2 (invention) |
|---|---|---|---|
| A | Arachidyl alcohol, behenyl alcohol and arachidylglucoside (Montanov 202 ®) | 3 | 1.5 |
| | Isopropyl palmitate (Dub IPP ®) | 10 | 5 |
| | Dimethicone (10 cSt) (Element14 PDMS 10-A ®) Isohexadecane | 10 | 5 |
| | Beeswax White beeswax (GR B 889 ®) | 3 | 1.5 |
| B | Hydroxypropyl starch phosphate (Structure XL ®) | 1 | 1.5 |
| | Steareth-100/PEG-136/HDI Copolymer (Rheolate FX 1100 ®) | 0.5 | 0.5 |
| C | Silica (Sunsphere H 51 ®) | 3 | 3 |
| D | 50% aluminium chlorohydrate solution (Chlorhydrol 50 ®) | 20 | 20 |
| | Water | qs 100 | qs 100 |
| | Preserving agents | 0.6 | 0.6 |
| G* (Pa) | | 18 000 | 9000 |
| Stability after 24 hours at 25° C. | | Stable | Stable |

These tubes make it possible easily to dispense, by pressing just once with the fingers, a correct dose with a thick formulation and to produce at the outlet in a uniform manner, both in terms of restitution (volume) and distribution, a product which combines an immediate dry, soft, non-wetting and non-tacky feel.

The invention claimed is:

1. A dispensing device and composition comprising:
   a) a container comprising a deformable wall, and
   b) a composition in the form of an oil-in-water emulsion stored in the container, and comprising, in a cosmetically acceptable medium:
      i) at least one aqueous phase, wherein the at least one aqueous phase represents from 10% to 90% by weight relative to the total weight of the composition, and
      ii) at least one oily phase, which is at least isopropyl palmitate and wherein the at least one oily phase represents from 10% to 90% by weight relative to the total weight of the composition,
      iii) at least one structuring agent in an amount of 2% to 20% by weight relative to the total weight of the composition; wherein the at least one structuring agent comprises
         polyurethane polyether,
         hydroxypropyl starch phosphate, and
         at least one of beeswax or silica
      iv) at least one antiperspirant active agent and/or one deodorant active agent; and v) at least a mixture of a nonionic surfactant and of a fatty alcohol selected from the group consisting of
a mixture of arachidyl alcohol, behenyl alcohol and arachidylglucoside,
a mixture of cetearyl alcohol and cetearylglucoside, and mixtures thereof;

said composition having a stiffness modulus G*>5000 Pa measured at 25° C. using a Haake RS600 imposed-stress rheometer equipped with a 60 mm diameter plate-plate measuring body fitted with a bell jar anti-evaporation device with the measurements starting 5 minutes after placing a sample of the composition in a 2 mm air gap and wherein the sample is subjected to a stress ramp from $10^{-2}$ to $10^3$ Pa at a set frequency of 1 Hz, and c) a dispensing head closing off the container and comprising an application wall defining at least one product dispensing orifice which is a slit.

2. The dispensing device and composition according to claim 1, wherein the at least one oily phase comprises at least one hydrocarbon-based oil; and the composition comprises
at least one wax with a melting point of greater than 45° C. comprising one or more $C_{40}$-$C_{70}$ ester compounds and not comprising any $C_{20}$-$C_{39}$ ester compounds.

3. The dispensing device and composition according to claim 2, wherein, in the composition, the wax is chosen from candelilla wax, rice bran wax, beeswax and sunflower wax, and mixtures thereof.

4. The dispensing device and composition according to claim 1, wherein each product dispensing orifice has at any point a smallest transverse dimension of less than 1.3 mm.

5. The dispensing device and composition according to claim 1, wherein the total extent of the orifices is less than 5% of the total extent of the surface of the application wall.

6. The dispensing device and composition according to claim 1, wherein the application wall is formed from a thermoplastic elastomer.

7. The dispensing device and composition according to claim 1, wherein the container is a deformable tube.

8. The dispensing device and composition according to claim 7, wherein the tube comprises a pocket.

9. A cosmetic process for treating and/or caring for human keratin materials, which comprises applying to the surface of the keratin material a composition dispensed via the device as defined in claim 1.

10. A cosmetic process for treating human perspiration and/or perspiration-related body odour, which comprises applying to the surface of a human keratin material a composition dispensed via the device as defined in claim 2.

11. The dispensing device and composition according to claim 1, wherein the composition has a stiffness modulus G*>8000 Pa.

12. The dispensing device and composition according to claim 1,
iii) wherein said at least one structuring agent comprises beeswax, silica, polyurethane polyether and hydroxypropyl starch phosphate.

13. The dispensing device and composition according to claim 1, wherein the total extent of the orifices is less than 2.5% of the total extent of the surface of the application wall.

14. The dispensing device and composition according to claim 1, wherein said dispensing device is adapted for dispensing said composition as a tube.

15. The dispensing device and composition according to claim 1, wherein the at least one aqueous phase represents from 30% to 90% by weight relative to the total weight of the composition; the at least one oily phase represents from 10% to 30% by weight relative to the total weight of the composition, the composition comprises a water-soluble polysaccharide in an amount of 0.5% to 6% by weight relative to the total weight of the composition and a hydrocarbon oil in an amount of 5% to 30% by weight relative to the total weight of the composition.

* * * * *